United States Patent
Moffitt et al.

(10) Patent No.: US 10,391,313 B2
(45) Date of Patent: Aug. 27, 2019

(54) SYSTEMS AND METHODS FOR THE DEVELOPMENT OF THERAPY PARADIGMS FOR NEUROLOGICAL TREATMENTS

(71) Applicant: BOSTON SCIENTIFIC NEUROMODULATION CORPORATION, Valencia, CA (US)

(72) Inventors: Michael A. Moffitt, Saugus, CA (US); G. Karl Steinke, Valencia, CA (US); Sridhar Kothandaraman, Valencia, CA (US); Bradley Lawrence Hershey, Valencia, CA (US); Changfang Zhu, Valencia, CA (US); Jordi Parramon, Valencia, CA (US); Goran N. Marnfeldt, Valencia, CA (US); John Rivera, Oxnard, CA (US); Stephen Carcieri, Los Angeles, CA (US)

(73) Assignee: BOSTON SCIENTIFIC NEUROMODULATION CORPORATION, Valencia, CA (US)

(*) Notice: Subject to any disclaimer, the term of this patent is extended or adjusted under 35 U.S.C. 154(b) by 0 days.

(21) Appl. No.: 15/367,491

(22) Filed: Dec. 2, 2016

(65) Prior Publication Data
US 2017/0157404 A1    Jun. 8, 2017

Related U.S. Application Data

(60) Provisional application No. 62/263,073, filed on Dec. 4, 2015.

(51) Int. Cl.
*A61N 1/36* (2006.01)
*A61N 1/372* (2006.01)
*A61N 1/05* (2006.01)

(52) U.S. Cl.
CPC ....... *A61N 1/36146* (2013.01); *A61N 1/0551* (2013.01); *A61N 1/36164* (2013.01);
(Continued)

(58) Field of Classification Search
CPC ................................................ A61N 1/36164
See application file for complete search history.

(56) References Cited

U.S. PATENT DOCUMENTS

| | | | |
|---|---|---|---|
| 6,083,248 A | 7/2000 | Thompson | |
| 6,385,593 B2 | 5/2002 | Linberg | |

(Continued)

FOREIGN PATENT DOCUMENTS

| | | |
|---|---|---|
| WO | 2010039274 A1 | 4/2010 |
| WO | 2013055940 A2 | 4/2013 |

(Continued)

*Primary Examiner* — Kennedy Schaetzle
(74) *Attorney, Agent, or Firm* — Seager, Tufte & Wickhem LLP

(57) ABSTRACT

Methods, devices and systems for developing new therapy options for patient suffering from neurological disorders. An example may include the use of a therapy patterning system that allows significant freedom to program therapy patterns using arbitrary shapes and functions. For such patterning to be implemented, a physician may identify a condition needing new and/or alternative therapy options, link the identified condition one or more therapy parameters, program, test and assess the therapy. The process may include multiple iterations to address an initial condition and then to mitigate side effects of the initial therapy. Some embodiments comprises devices configured to deliver combinations of therapy patterns to accomplish at least first and second therapeutic purposes.

20 Claims, 9 Drawing Sheets

(52) U.S. Cl.
CPC ..... *A61N 1/36185* (2013.01); *A61N 1/37241* (2013.01); *A61N 1/0534* (2013.01); *A61N 1/36062* (2017.08)

(56) References Cited

U.S. PATENT DOCUMENTS

| | | | |
|---|---|---|---|
| 6,442,432 B2 | 8/2002 | Lee |
| 6,480,745 B2 | 11/2002 | Nelson et al. |
| 6,564,104 B2 | 5/2003 | Nelson et al. |
| 6,577,901 B2 | 6/2003 | Thompson |
| 6,587,724 B2 | 7/2003 | Mann |
| 6,622,050 B2 | 9/2003 | Thompson |
| 6,644,322 B2 | 11/2003 | Webb |
| 6,648,823 B2 | 11/2003 | Thompson |
| 6,731,986 B2 | 5/2004 | Mann |
| 6,895,280 B2 | 5/2005 | Meadows et al. |
| 6,920,360 B2 | 7/2005 | Lee et al. |
| 7,060,031 B2 | 6/2006 | Webb et al. |
| 7,149,581 B2 | 12/2006 | Goedeke |
| 7,149,773 B2 | 12/2006 | Haller et al. |
| 7,177,699 B2 | 2/2007 | Fabian et al. |
| 7,447,549 B2 | 11/2008 | Litvak et al. |
| 7,685,005 B2 | 3/2010 | Riff et al. |
| 7,715,912 B2 | 5/2010 | Rezai et al. |
| 7,815,568 B2 | 10/2010 | Linberg et al. |
| 7,818,180 B2 | 10/2010 | Riff |
| 8,036,754 B2 | 10/2011 | Lee et al. |
| 8,108,033 B2 | 1/2012 | Drew |
| 8,355,798 B2 | 1/2013 | Lee |
| 8,412,345 B2 | 4/2013 | Moffitt |
| 8,428,731 B2 | 4/2013 | Armstrong |
| 8,437,857 B2 | 5/2013 | Moffitt et al. |
| 8,442,655 B2 | 5/2013 | Moffitt et al. |
| 8,447,405 B2 | 5/2013 | Grill et al. |
| 8,504,160 B2 | 8/2013 | Lee et al. |
| 8,543,200 B2 | 9/2013 | Lane et al. |
| 8,583,262 B2 | 11/2013 | Parramon et al. |
| 8,612,019 B2 | 12/2013 | Moffitt |
| 8,615,306 B2 | 12/2013 | Griffith |
| 8,660,655 B2 | 2/2014 | Peterson et al. |
| 8,676,308 B2 | 3/2014 | Moffitt et al. |
| 8,788,059 B2 | 7/2014 | Moffitt et al. |
| 8,795,755 B2 | 8/2014 | Lien et al. |
| 8,812,115 B2 | 8/2014 | Lee |
| 8,812,131 B2 | 8/2014 | Parramon et al. |
| 8,843,211 B2 | 9/2014 | Lee |
| 8,868,193 B2 | 10/2014 | Ranu et al. |
| 8,868,794 B2 | 10/2014 | Masoud et al. |
| 8,923,981 B2 | 12/2014 | Grill, Jr. et al. |
| 9,144,679 B2 | 9/2015 | Cullen et al. |
| 9,144,682 B2 | 9/2015 | Starobin et al. |
| 9,144,687 B2 | 9/2015 | Griffith et al. |
| 9,155,885 B2 | 10/2015 | Wei et al. |
| 9,155,892 B2 | 10/2015 | Parker et al. |
| 9,162,068 B2 | 10/2015 | Dronov |
| 9,174,053 B2 | 11/2015 | Zhu |
| 9,205,259 B2 | 12/2015 | Kim et al. |
| 9,211,408 B2 | 12/2015 | Machado |
| 9,242,095 B2 | 1/2016 | Grill, Jr. et al. |
| 9,259,579 B2 | 2/2016 | Grill et al. |
| 9,358,396 B2 | 6/2016 | Holley |
| 9,393,423 B2 | 7/2016 | Parramon et al. |
| 9,468,771 B2 | 10/2016 | Griffith et al. |
| 9,474,905 B2 | 10/2016 | Doan et al. |
| 9,561,380 B2 | 2/2017 | Carcieri et al. |
| 9,572,988 B2 | 2/2017 | Grill et al. |
| 9,623,250 B2 | 4/2017 | Lee et al. |
| 9,643,015 B2 | 5/2017 | Moffitt et al. |
| 9,974,961 B2 * | 5/2018 | Moffitt ................. A61N 1/0553 |
| 2005/0228693 A1 | 10/2005 | Webb et al. |
| 2008/0294226 A1 * | 11/2008 | Moffitt ................. A61N 1/0553 607/74 |
| 2013/0116929 A1 | 5/2013 | Carlton et al. |

FOREIGN PATENT DOCUMENTS

| | | |
|---|---|---|
| WO | 2014130071 A1 | 8/2014 |
| WO | 2016069157 A1 | 5/2016 |
| WO | 2016182894 A1 | 11/2016 |

* cited by examiner

SYSTEMS AND METHODS FOR THE DEVELOPMENT OF THERAPY PARADIGMS FOR NEUROLOGICAL TREATMENTS

CROSS REFERENCE TO RELATED APPLICATIONS

The present application claims the benefit of and priority to U.S. Provisional Patent Application Ser. No. 62/263,073, filed on Dec. 4, 2015, the disclosure of which is incorporated herein by reference.

BACKGROUND

Implantable and/or wearable stimulations systems for the treatment of various diseases and disorders of the neurological system have proven effective in a wide variety of ways. For example, spinal cord stimulation (SCS) systems are accepted treatments for chronic pain syndromes. Deep brain stimulation (DBS) systems have been used for chronic pain as well, and are gaining acceptance for treatment of movement and tremor disorders. Peripheral nerve stimulation (PNS) systems have also been shown effective for certain indications, and functional electrical stimulation (FES) has been investigated for restoration of functionality to paralyzed extremities. These and other therapies are under investigation for numerous indications beyond those already in use.

Historically many of the available hardware systems facilitated a limited variety of therapeutic output waveforms, such as voltage or current controlled square waves. A proposed new hardware and/or embedded software arrangement will remove some of the existing limitations on waveform type to yield more flexible systems. Therefore it is desirable to identify and develop new approaches to the use of more flexible systems to identify and provide new therapy paradigms.

OVERVIEW

Methods, devices and systems for developing new therapy options for patient suffering from neurological disorders. An example may include the use of a therapy patterning and waveform selection system that allows significant freedom to program therapy patterns using arbitrary shapes and functions. For such patterning to be implemented, a physician may identify a condition needing new and/or alternative therapy options, link the identified condition one or more therapy parameters, program, test and assess the therapy. The process may include multiple iterations to address an initial condition and then to mitigate side effects of the initial therapy. The process may also include identifying features of a neural network, identifying signals within the network, and modulating operation of the network, and/or parts of the network. Some embodiments comprise devices configured to deliver certain therapy patterns and combinations as well.

This overview is intended to briefly introduce the subject matter of the present patent application, and is not intended to provide an exclusive or exhaustive explanation of the invention. The detailed description is included to provide further information.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
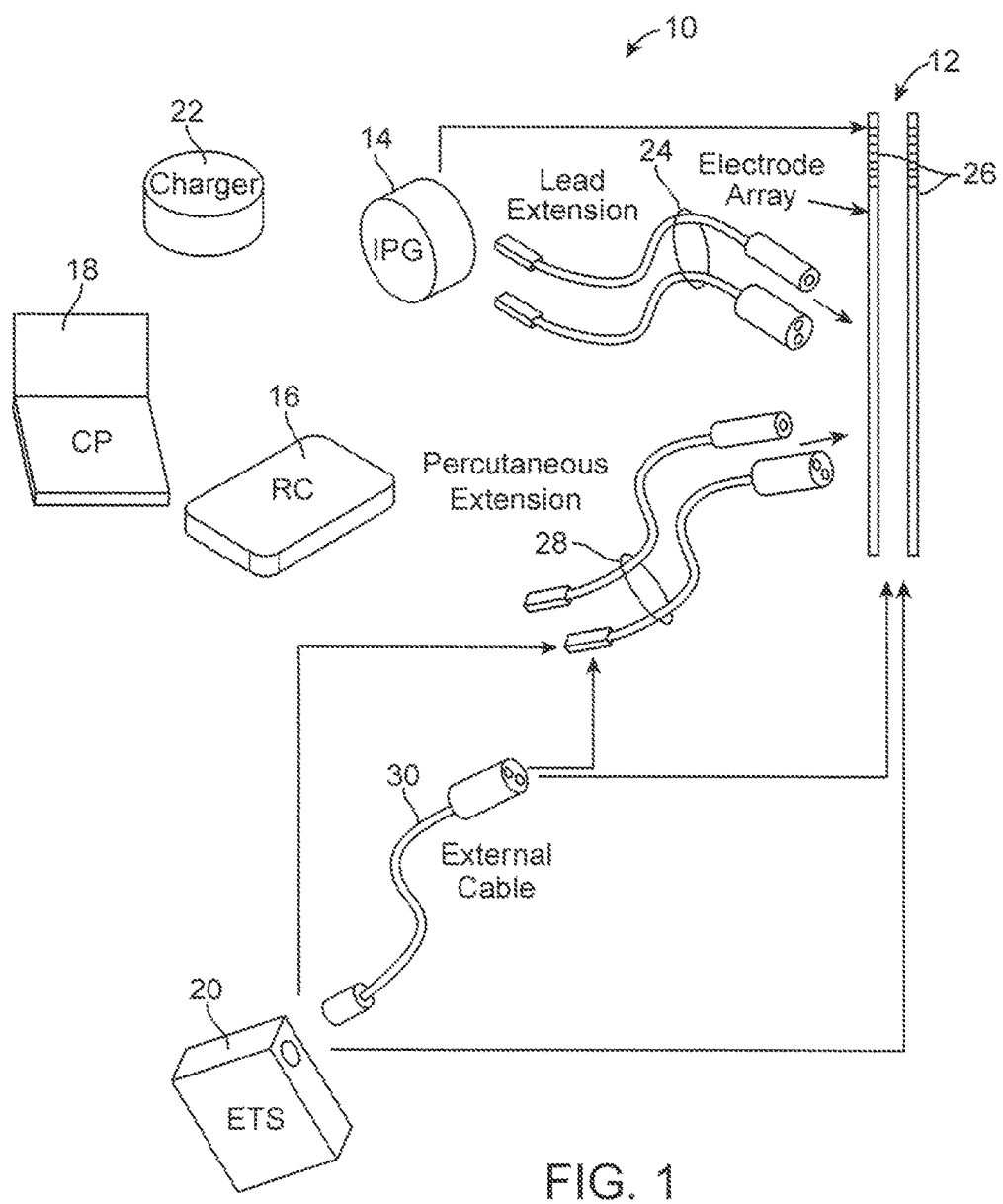
FIG. 1 shows various functional components of an illustrative neurostimulation system.

FIG. 1 shows a system for providing neurological therapy, for example, as spinal cord stimulation (SCS), deep brain stimulation (DBS), peripheral nerve stimulation (PNS), or functional electrical stimulation (FES). The system 10 includes electrodes 12 configured for coupling to an implantable pulse generator (IPG) 14. The IPG may communicate with one or more of a patient remote control (RC) 16, a clinician programmer (CP) 18, and/or a charger 22. An external testing system (ETS) 20 may also be provided for testing therapy parameters prior to implantation of the IPG, using percutaneous extensions 28 and, as needed an external cable 30 to couple to the implantable electrodes 12. If needed, lead extensions 24 may be used to couple the IPG to the implantable electrodes 12.

As shown in FIG. 1, the implantable electrodes may include arrays of electrode contacts on linear leads 26; in other examples, paddle leads may also be used. One, two or even four leads 12 may be provided, with up to 32 total contacts available in modern systems; in the future more or fewer contacts on more or fewer leads may be provided depending the particular system.

The IPG 14 can couple directly to the electrodes 12 or may be coupled via the lead extensions 24, depending on the positioning of each element as implanted. The IPG may include a rechargeable battery and charging coil to allow recharging when placed in proximity to the charger 22. Alternatively, the IPG may use a non-rechargeable battery and omit the charging coil. In some examples, the IPG may be externally powered and omits a battery entirely.

The CP 18 can be used by a physician to manipulate the outputs of the IPG 14 and/or ETS 20. For example the CP 18 can be used by the physician to define a therapy regimen or program for application to the patient. Multiple programs may be facilitated and stored by the IPG 14 or ETS 20; in some examples, the RC 16 may store the programs to be used. Communication amongst the IPG 14, RC 16, CP 18, ETS 20 and Charger 22 may use any suitable protocol such as wireless RF telemetry, inductive communication, Bluetooth, etc.

The RC 16 may be used by a patient to enable or disable therapy programs, to select between available programs, and/or to modify the programs that are available for use. For example, in some embodiments a patient may use the RC 16 to activate a stored program and then manipulate therapy by increasing or decreasing therapy strength and/or changing therapy location, within limits set by the physician.

Figure 2:
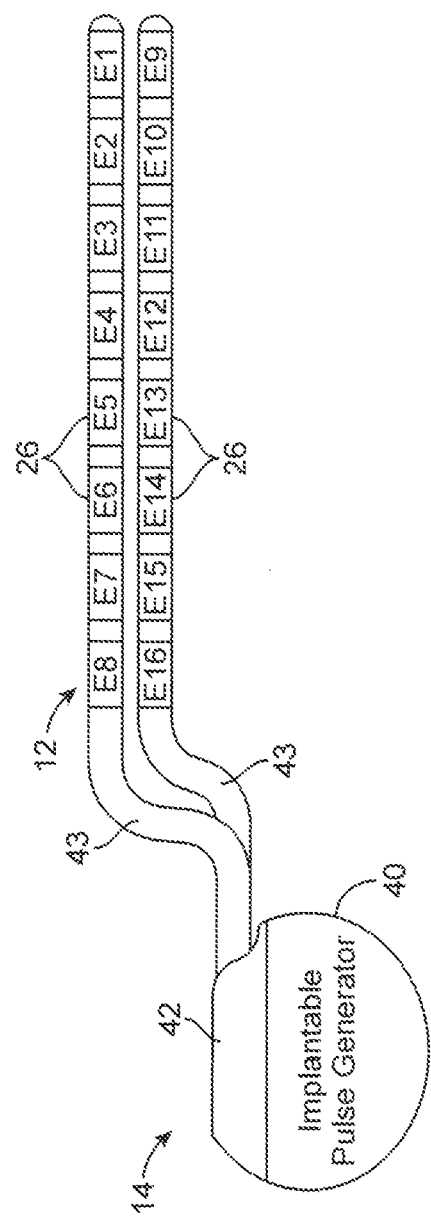
FIG. 2 shows an implantable stimulator and electrodes.

FIG. 2 shows an implantable stimulator and electrodes. As shown in the closer detail here, the IPG 14 may include a canister 40 and header 42. The canister 40 is conductive in most examples, using biocompatible materials such as titanium and/or stainless steel, for example, to allow use as an electrode when implanted. The header allows removable connection to the lead 12, which in this example may have a bifurcation or yoke allowing two segments 43 to extend therefrom, to two arrays 26 at the distal end of the lead 12. The electrode arrays 26 can be numbered as shown to facilitate ease of understanding when programming, with, for example, one array marked electrodes E1 to E8 on one of the lead segments 43, with E1 being distalmost. Other conventions may be used.

Figure 3:
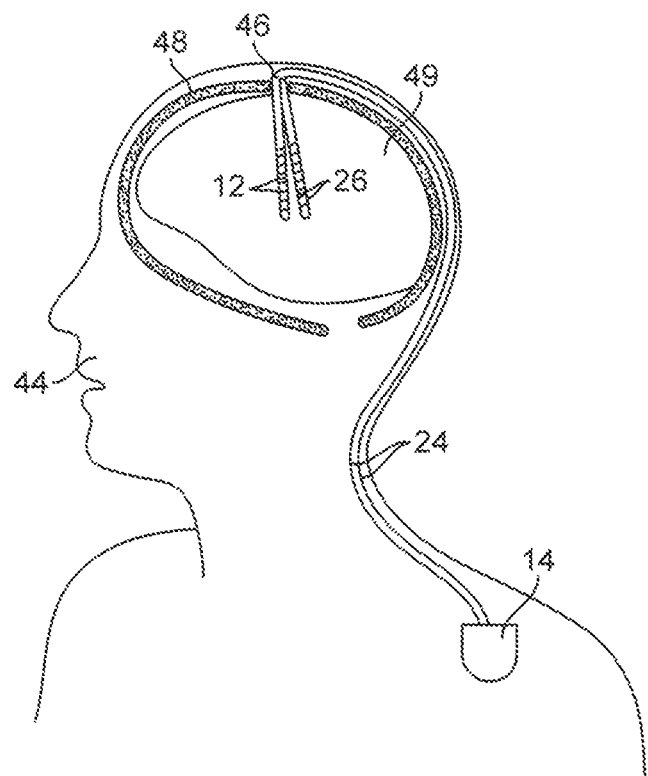
FIG. 3 shows an illustrative deep brain stimulation system as implanted.

FIG. 3 shows an illustrative deep brain stimulation system as implanted. The IPG 14 may be implanted in the patient's upper chest or neck region, with a lead extension 24 going up the neck to the head. The lead 12 is inserted through an anchor 46 that can be placed in a burr hole formed through the cranium 48 of the patient, allowing the arrays 26 at the distal end of the lead 12 to be placed inside the brain 49. The procedure can be performed using known visualization techniques and technologies so that the electrodes on lead 12 may be placed in proximity to a desired structure for therapy. Other locations the IPG 14 and/or lead 12 may be used.

Figure 4:
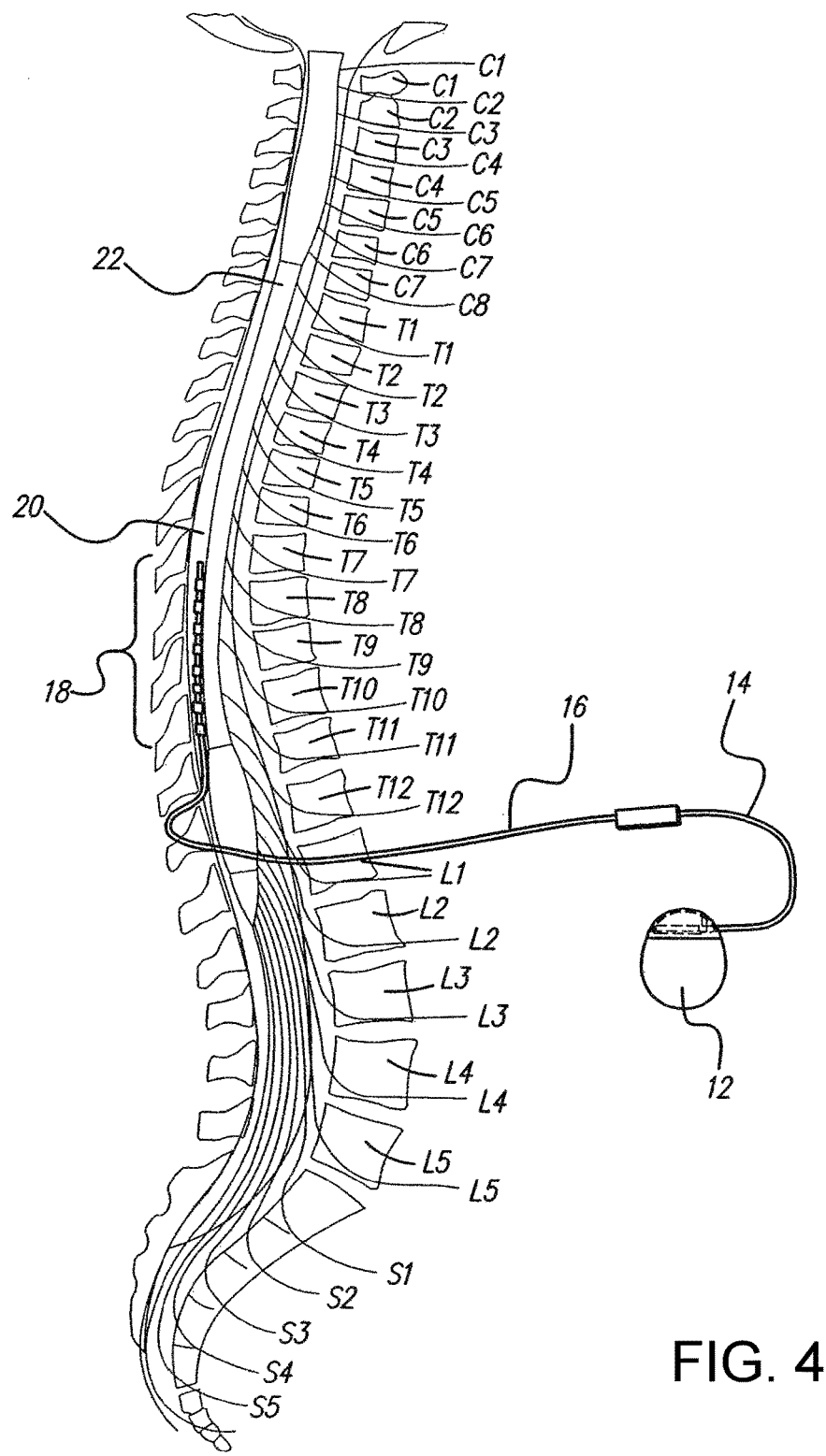
FIG. 4 shows an illustrative spinal cord stimulation system as implanted.

FIG. 4 shows an illustrative spinal cord stimulation system as implanted. In this example, an IPG 50 may be placed near the buttocks or in the abdomen of the patient, with or without a lead extension 52 for coupling to the lead(s) 54 that enter the spinal column. Region 56, at about the level of the lower thoracic or upper lumbar vertebrae may serve as an entry point to the spinal column, where the distal end of the lead 54 with an electrode array may be placed close to the spinal cord 58. Other locations for the IPG 50 and/or lead 54 may be used.

The standard approach to therapy in systems similar to those shown in FIGS. 1-4 has been that the IPG 14 (and ETS 20) may offer current controlled or voltage controlled therapy comprising either biphasic square waves or monophasic square waves having passive recovery. In general, the amount of current out of an electrode should zero out over time to avoid encouraging corrosion at the electrode-tissue interface. For this reason, biphasic pulses, or monophasic pulses with a passive recovery period are typically used. In prior systems, rather immediate compensation is performed to zero the charge remaining on any given electrode interface by incorporating a biphasic waveform of equal anodic and cathodic portions, or by providing passive of charge between sets of therapy outputs.

An individual component of a therapy program, in these systems controls a subsequent component or impulse. For example, when delivering a biphasic square wave therapy, the duration and amplitude of the first phase controls the duration and amplitude of the second phase, in order to achieve charge balancing. In a monophasic therapy with passive recovery, again, the duration and amplitude of the active phase ultimately determines the length and strength of the recovery signal applied thereafter. In some examples, the present invention does away with this limiting approach to therapy delivery by allowing arbitrary functions to be achieved within a therapy program, while applying rules for charge balancing, duty cycle and the like, across the program rather than on a pulse-to-pulse basis. With greater flexibility, a physician will be able to use the system to accomplish more varied waveforms. As a result, the physician is allowed to take further steps in the development of new therapy waveforms for new therapy indications. Much of the following discussion focuses on how physician may use this new capability.

More recent launches by some companies, and ideas still in development, include the concepts of burst stimulation and high frequency stimulation. Burst stimulation is merely the provision of a concatenation of biphasic pulses end to end, provided in short "bursts" at intervals. For example, burst therapy may deliver 500 Hz square waves may be delivered for 5 cycles, with the sets of 5 cycles repeated every 25 milliseconds (40 Hz). High frequency stimulation, for example, at 10 kHz, is simply the same therapy offered at high rates. While these options are available using the flexible architecture described herein, neither is as flexible as the therapy described and shown herein. The wider variety of variables may facilitate therapy development paradigms that are further described below.

Figure 5:
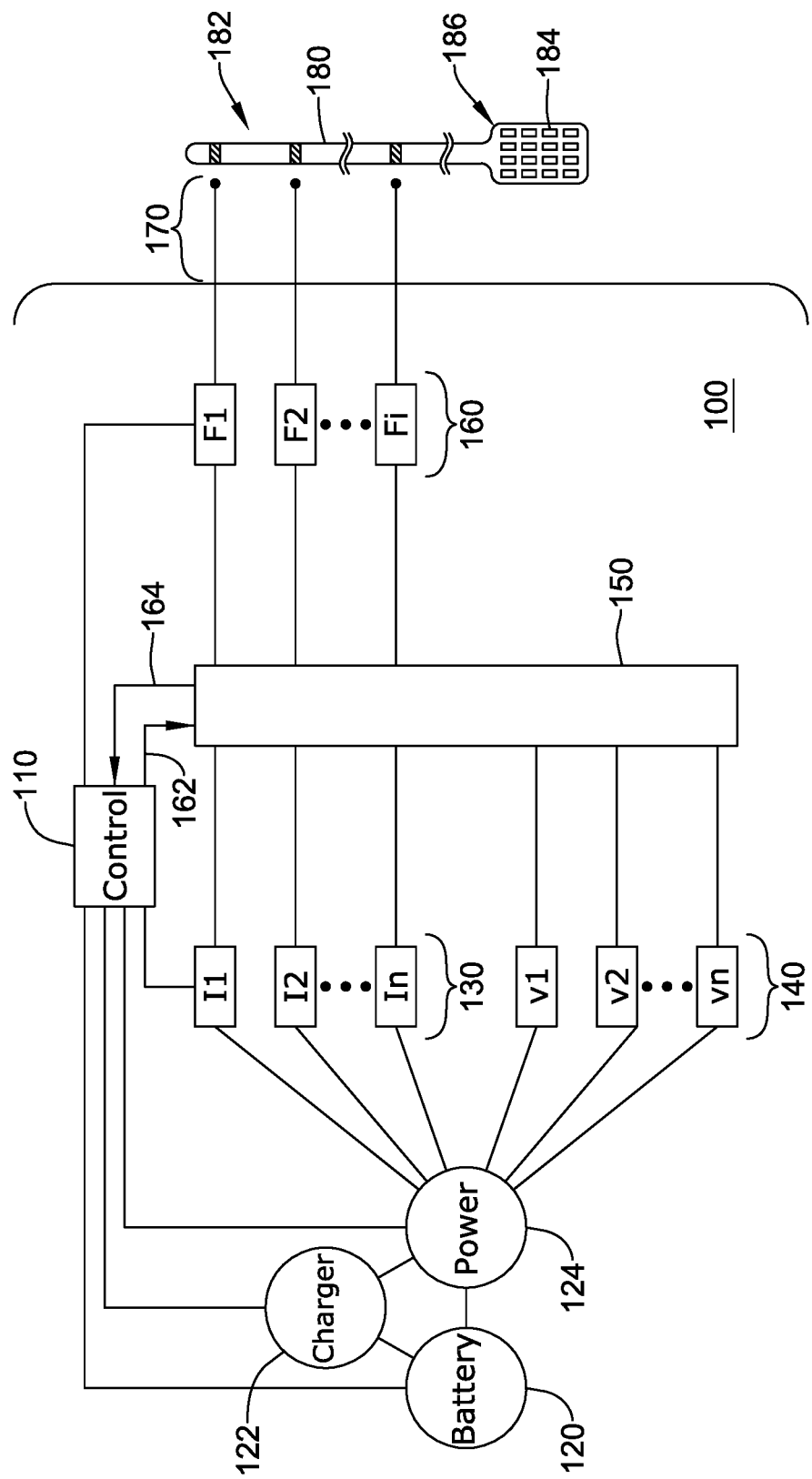
FIG. 5 shows an output architecture for an illustrative pulse generator.

FIG. 5 shows an output architecture for an illustrative pulse generator, which may be implantable or external. The device 100 includes a control block 110. The control block 110 may be implemented as a microcontroller or microprocessor, with associated memory banks to store instruction sets to be implemented as appropriate/needed, and/or data for later recall. In other examples, the control block 110 may be implemented as a state machine, or as a combination of circuits including, for example, various logic and memory circuits and analog, mixed signal, or digital application specific integrated circuit (ASIC) components. The control block may include suitable analog to digital conversion circuitry and, if desired, digital signal processing circuits. Though not shown the device 100 may be include telemetry and other circuitry to perform various well known functions such as communicating to an affiliated programmer and/or remote control.

A battery 120 may be used to provide power to the system, and may be coupled to a charger 122 if the battery is rechargeable. In some examples, a non-rechargeable battery 120 is used and the charger 122 can be omitted. As another alternative, the battery 120 may be omitted and the system may be operable when the charger 122 receives external power.

A power unit 124 is also shown. The power unit 124 may provide various power outputs to support therapy driving circuitry that can include a plurality of current controlled sources 130 and/or voltage controlled sources 140. Single or plural sources 130/140 may be provided, and any number of each can be used. In other examples, the sources may be convertible between voltage or current supply. The sources 130/140 may be fixed or variable. To support a variety of sources, the power unit 124 may have voltage controlled output lines, for example, 3, 5 or 15 volt supply lines (or other voltage level), and/or one or more compliance voltage sources (using for example a capacitor coupled to a voltage multiplier or booster) that maintains adequate headroom to drive the current sources 130. Various implementations for each of elements 120, 122, 124, 130 and 140 can be used.

An output controller 150 couples the sources 130/140 to output filters 160 and contacts 170 for coupling to a lead 180 or lead extender (not shown). The output controller 150 may simply connect a dedicated source or sources 130/140 to a single output 170 via hardwire or via switches, or, in other implementations, may multiplex the various sources 130/140 to various outputs by including a multiplexor or switch array.

The plurality of filters 160 may be dedicated to each of the outputs 170, as shown, or may instead be switchable in and out of association with the individual outputs 170, or may be omitted entirely depending on the nature of the output controller 150 and/or sources 130/140. The microprocessor 110 may control the filters 160, as shown, as well as the sources 130/140 and output controller 150. If sensing capability (sometimes referred to in particular for neurological therapy including neurostimulation or neuromodulation as closed loop) is provided, the microprocessor 110 may not only have a control line 162 to the output controller 150, but may receive signals on a sensing line 164. The sensing line 164 may instead be linked directly to the contacts 170.

The contacts 170 may be provided in a header (not shown) for coupling to the lead 180. One or more contacts 170 may couple to the housing of the device 100 which may serve as one or more electrodes for use in the patient. For example, button electrodes may be provided on the device 100 and/or a large portion of the device housing may serve as a single large electrode.

The lead 180 includes a plurality of spaced apart contacts 182 for coupling to contacts 170. In this example, the lead is shown as having electrodes 184 at its distal end arrayed on a paddle 186. A plurality of leads 180 may be used. The lead 180 may instead be coupled to the device 100 using a lead extension. The lead 180 may also take the form of a split lead having a yoke and multiple paddles 186 or other distal structures having electrodes thereon. In one example, rather than a lead, an ultrasound, RF or other energy output may be provide to activate remotely located electrodes.

FIGS. 6-11 show several illustrative therapy patterns. Historically, a square wave output would be provided by closing a switch or turning on a given output at a specific level; for a more complex, non-square wave output, other approaches may be taken. It should be noted that the signals shown may be configured as voltage controlled or current controlled outputs. In either case, a digitized output may provide sequential individual outputs at given levels to approximate a curve. Alternatively, for a controlled current curve, a current mirror may be coupled to analog circuitry that provides a controlled voltage across a resistor, generating a current output through the resistor which can then be copied using the current mirror to develop a controlled current output. For a controlled voltage curve, an analog circuit may be configured to generate a desired curve and a resultant voltage passed through a buffering amplifier (or gain amplifier) to provide the output.

Figure 6:
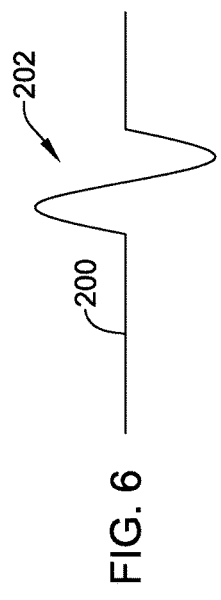

FIG. 6 shows, as an example, a single cycle of a sinusoidal therapy pattern. Output 200 remains at essentially zero until the sinusoid is delivered at 202. In one example, the sinusoid 202 is made up of a series of individual steps and is basically a digital approximation. In another example, one or more of the sources within a device may be configured as an analog sinusoid (for example, a driven RC circuit having a controllable frequency by virtue of making the resistor or capacitor of the RC circuit variable coupled to a buffer/amplifier), and the output is switched on for the analog sinusoid.

Figure 7:
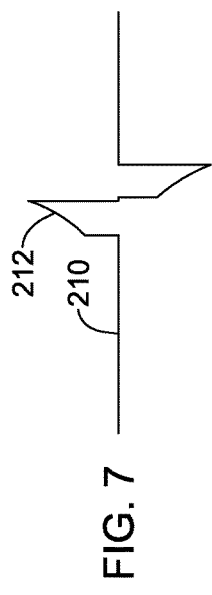
FIGS. 6-11 show several illustrative therapy patterns.
Figure 9:
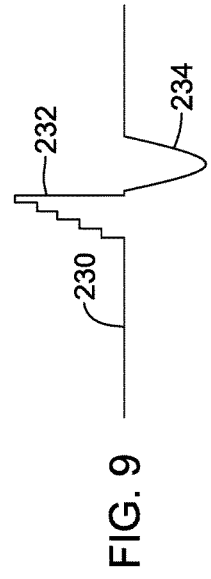
Figure 8:
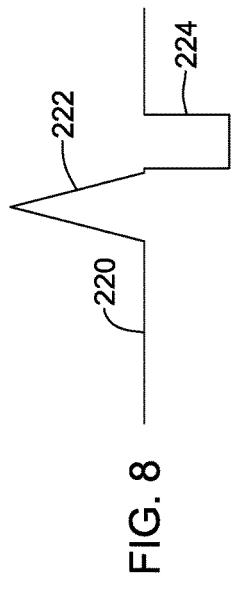
Figure 11:
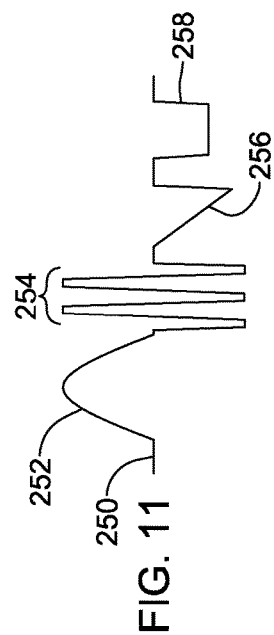
Figure 10:
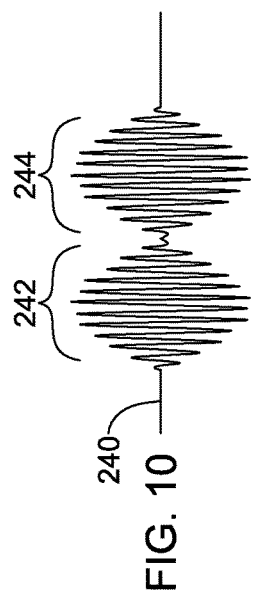

FIG. 7 shows another example in which an up-ramped exponential function is provided, with the signal 210 at zero until the function 212 is applied. FIG. 8 shows an output 220 with up and down ramps (a triangle wave) at 222, followed by a square wave 224. FIG. 9 shows an output 230 with a stepped output 232 followed by a sinusoidal half-cycle 234. FIG. 10 shows an amplitude modulated carrier signal with first cycle 242 and second cycle 244. FIG. 11 shows a longer script in which an output 250 includes a sinusoidal half wave, followed by a short burst, a ramp 256 and a square wave 258.

FIG. 11 shows a longer script in which an output 250 includes a sinusoidal half wave 252, followed by a short burst 254, a ramp 256 and a square wave 258. Other combinations may be provided, with different components of the waveform having different internal purposes. For example, a high frequency burst 254 in FIG. 11 may serve a purpose of minimizing the sensation of paresthesia (the tingling sensation associated with standard SCS) to a patient, while a square wave 258 may be provided to block a pain signal.

Assuming delivery by a single pair of electrodes, each of FIGS. 6-11 are shown with approximately balanced anodic and cathodic outputs; this need not be the case in all examples but is likely typical. However, different elements of the pattern shown in FIG. 11 may be generated across different electrode combinations. For example, assuming delivery by a system as shown in FIG. 2, the sinusoidal half wave of FIG. 11 may be delivered via a selected pair of electrodes 26 (for example, E11 as anode and E2 as cathode), followed by the high frequency burst 254 via a different selected pair of electrodes 26 (for example, between E10 and E7), with the ramp 256 delivered via yet another pair (E3 and E4), and the square wave 258 delivered across a different combination (E2 and E4 as anodes, and E11 as cathode).

As more complex patterns develop, several rules for charge balancing electrode interfaces may also be developed to ensure that short term, long term, and intermediate term rules to avoid encouraging electrode interface degradation/corrosion are avoided. For example, a first rule may be that the long term, average charge on an interface be zero—thus, over a period in the range of about ten minutes to twenty-four hours, the amount of current through a single interface should balance out to zero. A second rule may be that the mid-term period in the range of about one second to about ten minutes, average charge on an electrode interface of a given size and material be less than a preset quantity (i.e., no more than 10 milli-coulombs), which may be determined by tracking current and time period for each electrode interface. Finally, short term rules may call for a maximum cumulative quantity of current through an electrode interface in the near term, such as less than 10 seconds, and/or a maximum instantaneous current or voltage.

While the short term rules and long term rules may already be understood for existing systems with limited capabilities, the intermediate term rules may be more pertinent with more complex waveforms and patterns. Intermediate term rules may also take the form of a curve or set of curves, for example, a maximum charge burden may be defined as the amount of charge held over time on an interface, and may be subject to a set of rules for different time periods. In an example, a maximum quantity of charge to hold may be defined for periods of one second, five seconds, and ten seconds, with the maximum charge decreasing as the period of time increases.

As a result of such rulesets, a pattern as shown in FIG. 11 and described above may include a first portion, as shown, which is the therapeutic design, and a second portion applicable across the various electrodes to address intermediate term and long term rules, with the second portion designed to apply at sub-threshold levels to avoid paresthesia, for example, or other stimulus, while balancing out charge on the electrode interfaces.

In addition to electrode-interface protective rulesets, various safety rulesets may be enforced. For example, a maximum therapy amplitude may be system hardware limited or may be limited according to concerns for potentially causing tissue damage. Minimum periods between therapy outputs maybe required. There may also be limits placed on duty cycling and charge density, for example.

Other combinations may be provided, with different components having different internal purposes. For example, a high frequency burst 254 in FIG. 11 may serve a purpose of minimizing the sensation of paresthesia (the tingling sensation associated with standard SCS) to a patient, while a square wave 258 may be provided to block a pain signal.

Each of FIGS. 6-11 are shown with approximately balanced anodic and cathodic outputs; this need not be the case in all examples but is likely typical.

Figure 12:
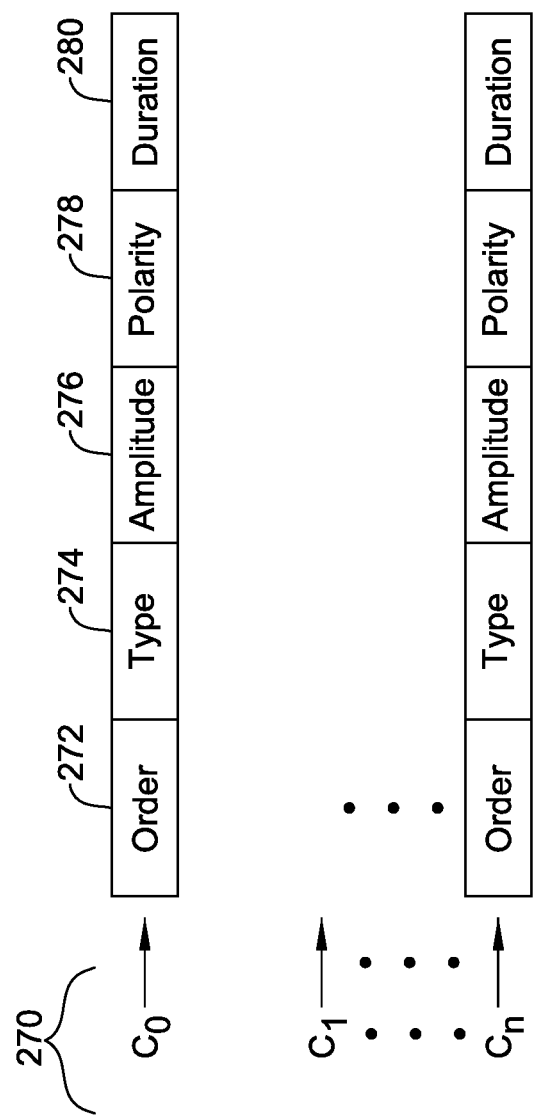
FIGS. 12 and 13 show how a therapy pattern may be stored and/or executed.
Figure 13:
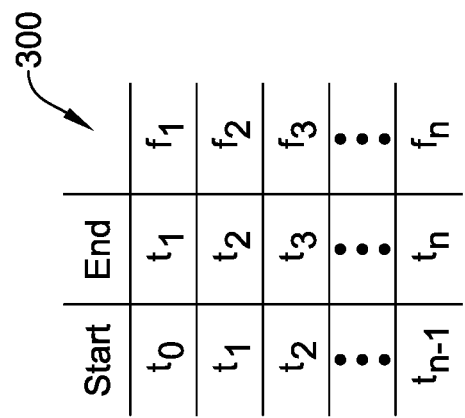

FIGS. 12 and 13 show how a therapy pattern may be stored and/or executed. Referring first to FIG. 12, a therapy may be provided essentially as a script of sequential commands. The commands may be numbered as shown at 270 [$C_0 \ldots C_n$], for example. Each command can include an indication of its order 272 within a sequence. The command can include an indication of type 272 which may determine whether a voltage controlled output or a current controlled output is to be provided. Type 272 may also indicate which electrodes are to be used in delivering the output. Type 272 may include a shape determination as well, such as whether a fixed, ramped, curved, sinusoidal, or exponential output is to be generated. The peak amplitude 276 may be indicated, as is polarity 278 (which may instead by a subcomponent of type, if desired), and duration 280. As a group these elements may be stored as a memory structure or object. A detailed example of storing of a therapy pattern may be found as well in U.S. Pat. No. 9,144,687, the disclosure of which is incorporated herein by reference.

For example, an approximation of a sinusoid may be provided as a series of individual outputs with varying amplitude 276 that rises, falls, and rises again, to mimic the curvature of the sinusoid. In another example, an exponential output function may be designated with start and stop points and a curve definition indicating, for example, the time constant of the exponential. In another example, a sinusoidal function may be provided by a single element, for example, $C_0$ may comprise a type element 274 indicating the frequency of the sinusoid, the duration 280 indicating the number of cycles, or fraction of a single cycle to be implemented, polarity 278 indicating the leading polarity, and the amplitude 276 defining the peak amplitude.

FIG. 13 shows another manner of representing a therapy pattern. In this example, a given device may make available a function set that can be called, with each function set reliant on one or more parameters. In the example, a table 300 represents a therapy pattern having an overall duration of $t_n$ less $t_o$, in which functions $f_1$ to $f_n$ are used for durations defined by intermediate time points $t_1 \ldots t_{n-1}$. The individual functions may be data types defining sets of variables. For example, if function $f_1$ is a square wave, it may require inputs of amplitude, duration, and polarity. If function $f_2$ is a ramp, it may require inputs of starting amplitude, end amplitude, duration, and polarity. If function $f_3$ is a sinusoid, it may require inputs of frequency, amplitude, leading polarity, and cycle fraction/quantity. Other or additional functions may be provided. A null function may be provided, and functions may be callable in voltage or current modes. The set of functions is called in an order and for durations defined by the table 300.

Figure 14:
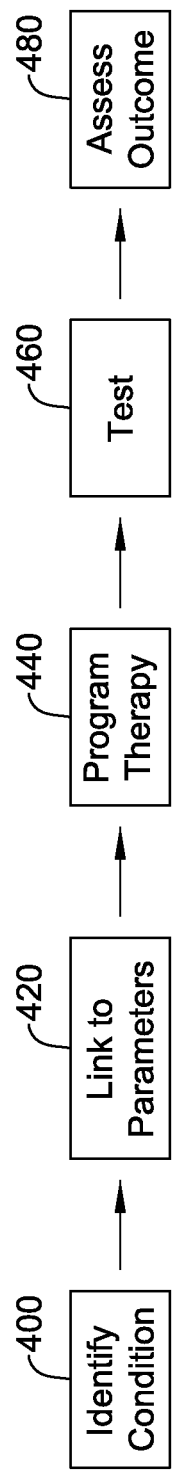
FIG. 14 shows an illustrative method in block flow form.

FIG. 14 shows an illustrative method in block flow form. The purpose in FIG. 14 is to plot out a manner in which a physician may develop a new therapy pattern to treat a given patient condition. A physician may identify the condition of the patient needing treatment, as indicated at 400, and then link the condition to therapy parameters, as indicated at 420. This linkage can be established using various approaches.

For example, in order to therapeutically affect a given cell type, a minimum electric field may be required to have a desirable affect upon a particular cell type that has been identified as responsible, contributing to, or a potential target for mitigating a given condition in its own right, or a side effect of therapy. As used herein, therapeutic affect or effect is a response that is desired and/or intended; a side effect is generally anything that is neither desired nor intended.

A method may include, for example, measuring (in vivo or in vitro, for example), or determining through analysis (using known qualities of the cell such as response to hormonal or drug interaction, or knowing the receptors of a cell such as calcium receptors) a known field level that can cause a response, will provide a link between a parameter and the identified condition. Within the context of neurological therapies for various conditions in the central nervous system (CNS), peripheral nervous system (PNS), and/or sympathetic nervous system (SNS), a number of cell types or cell components may be relevant. For example, cell bodies, axons, dendrites and ion channels may serve as the target for a given cell type, while relevant cell types may include not only neurological cells, but also glia, blood vessel cells, cells of the sympathetic nervous system, cells that generate inflammatory response, etc.

Desirable responses from cells and systems may take many forms. For example, a given cell may be stimulated in a manner directed toward various states such as, for example:

Hyperpolarization, in which a cell is stimulated in a manner to increase the needed stimulus to achieve depolarization and induce an action potential from a cell;

Stasis, the unexcited state of a cell, to which therapy delivery may drive an otherwise excited cell membrane;

Stimulated in a sub-threshold manner, in which a cell is stimulated away from stasis and toward excitation, but without reaching an action potential threshold;

Excited, in which input stimulus, from within the neurological system or artificially applied has caused a cell membrane to depolarize;

Refractory, following excitation, in which a cell is non-responsive until it has recovered from excitation; and Blocked, which may be thought of as a special form of refractory, where the cell has been stimulated in a manner that forces closure of certain uptake channels (typically the sodium channels) to extend refractory; blocking may be induced using high frequency signals, for example.

Any of these may be useful, alone or in various combinations, to assist in the treatment of a neurological condition. Any of these effects may be referred to as modulating the behavior of a cell, or cell population, in the context of delivered stimulus.

In one example, a systemic therapy concept may be pursued using one or more of exploratory testing, observation, and model formation, to generate a concept for the overall neurological network, in which signals and hence information pass back and forth. Upon identification of network response to pathological or otherwise abnormal internally or externally generated signals, the various "nodes" within a given neurological network may receive therapy. Such therapy may be provided to block, modulate, or alter a signal that would otherwise pass through a network.

Therapy may be generated so as to achieve a spatial effect—addressing different physical portions of the neurological network simultaneously or in ordered fashion. In some examples, a single system-wide therapy may be delivered to essentially reset a system. In other examples a local therapy may be applied to interrupt a signal propagation in a manner that disrupts pathological activity. In another example, a first location may receive therapy, for example, a sub-threshold therapy, to reduce a likelihood of propagation of an unwanted signal, while a second location receives therapy to hyperpolarize a region of tissue to impair propagation should it pass through the first location, while a third therapy is delivered to excite and create action potentials at a third location to limit the production of the pathological signal. Locational control may be determined in part by the use of current controlled output pulses having specific shape characteristics. In another example a timing scheme may be used to affect different structures in desirable sequences by, for example, providing a sub-threshold stimulus to a first location, then providing a stimulating stimulus at a second location, followed by additional sub-threshold stimulus again to the first location, where the sub-threshold stimuli are intended to mitigate propagation caused by the excitatory stimulus.

The tissue in many instances will include biological cells, the excitation of which is controlled largely by ion channels such as the sodium ion channels. Generally speaking cellular membranes maintain a level of stasis which can be disturbed by electric fields that can trigger activation once a threshold potential is reached. Different cells within the body, particularly different cell types, have different action potentials and may respond to different stimulation frequencies in different manners as well. In short, the environment is not homogenous. As a result, understanding the biological characteristics, in particular the susceptibility and immunity of individual cells to activation by electrical fields of specific frequency and amplitude characteristics—and in some cases, direction of propagation—can serve to link a target tissue to a therapy that may be useful for the target tissue. Such biological characteristics of cell types can be the link to therapeutic effectiveness.

Complex combinations may call for an asymmetric therapy delivery that allows polarization, temporarily, of an electrode interface until a later step for removing polarization is performed. For such a therapy approach, the following sequence may occur:
  (Optional) Initial pulse (asymmetric)
  Therapy pulses (asymmetric)
  Corrective, closing pulse(s) (asymmetric)
Such that the long term polarization of electrode interfaces is avoided, while not forcing upon the designing user polarity-neutral requirements on the therapy pulses themselves. The corrective, closing pulse(s) may be determined by tracking usage of each electrode during the therapy pulses. The corrective, closing pulse(s) may be delivered in a sub-threshold or hyperpolarizing manner, as needed.

In one example, using reference to FIG. 2, a hyperpolarizing stimulus is provided in a first, narrower spatial range (for example, with E5 as cathode and E6 as anode), followed, close in time, by a second stimulus at wider range (for example, with E4 as anode and E7 as cathode), such that the region close to E5 and E6 is less likely to respond to the second stimulus due to hyperpolarization caused by the first stimulus. This therapy may be repeated several times. After several repetitions, each of E4, E5, E6 and E7 will have charge stored at the tissue interfaces thereof, and so a set of corrective pulses at subthreshold or in hyperpolarizing manner may be delivered, for example, by delivering simultaneous outputs with E4 and E6 as cathodes, and E5 and E7 as anodes, until the net current for the set of outputs at each electrode is zero.

In another example, a device, such as a CP, may be configured to provide outputs to a physician indicating the predicted fields generated by certain combinations of electrode outputs. The physician, to link a therapy output to a therapeutic effect, may need to develop and/or understand a set of curves for different pairs of electrodes that allow a desired field to be effected at a desired distance from the electrodes. For example, if the goal is to have a field of 30 millivolts per centimeter at a distance of 2 centimeters from a paddle electrode, such a field could be generated with any of a number of different electrode pairs, some far more readily than others. Two immediately adjacent electrodes 1 centimeter apart may need to provide a different output than two electrodes 10 centimeters apart, and if a target is placed at a position out of alignment with an axis drawn between to electrodes, the field output may have to be further modified. Using more than two electrodes can spread or focus the field generated in various ways as well.

In another example, the parameter link 420 may also include an understanding of secondary responses. For example, simply knowing what field level may excite a given cell to cause that cell to become refractory at a desired time, or to generate an output signal for transmission, is sometimes only the first piece of the linkage at 420. In an embodiment, after determining a primary field needed to achieve a desired response from a targeted cell, a second therapy output may be generated to minimize side effects of the primary field. This may include, for example, mixing two types of therapy. A current controlled impulse may be used to target a desired cell structure at a desired location—since current controlled outputs can facilitate narrowly tailored fields—and may be followed and/or preceded by a voltage controlled output to place a larger, and less specific region of nerve tissue into a desired state. In one such example, referring to FIG. 2, electrodes E2 and E10 as cathodes and electrodes E4 and E12 as anodes for a single polarity output pulse), followed by a current controlled biphasic output using electrode E3 as anode and electrode E11 as cathode in the leading phase, followed by a recovery outputs using E2 and E10 as anodes and electrodes E4 and E12 as cathodes for a single polarity output pulse.

In another example, a physician or researcher may engage in an iterative testing process in which a therapy's primary purpose may be gleaned and addressed in a first pass, developing the therapy itself, and then testing various approaches to reducing side effects with subsequent testing. For example, a first testing may be done to prove that the original problem for which therapy is applied can be address, thus, in a hypothetical, a patient's pain sensation may be first addressed with therapy delivery, causing side effects such as paresthesia. Multiple secondary therapies may then be applied to determine effects on the paresthesia in order to reduce or eliminate it.

In another example, a primary therapy may be developed to identify parameters, with additional pre-therapy testing performed, for example, to determine ways to optimize the effect of the therapy to be delivered. In an example, an impulse is determined to address a movement disorder or tremor, and pre-pulsing may be tested to determine whether the impulse amplitude may be lowered, for example, to reduce power consumption or side effects. A number of additional illustrations are outlined below.

In another example, plural structures for therapy receipt are identified and plural therapies generated for affecting such structures. For example, with a multiple independent current control system, a first set of electrode outputs may be used to generate a first desirable field away from the electrodes to affect a first structure, and a second set of electrode outputs may be used to generate a second desirable field closer to the electrodes. The two outputs maybe alternated or simultaneous. In an alternative, two therapies may be delivered to a single neurological structure at different times within a pattern, such as providing a signal that generates both subperception therapy and supraperception therapy to generate paresthesia at a single locus such as at a location for desired paresthesia, at a dorsal horn stimulation (DHS) site, and/or at some other anatomical locus. In another example, a combination of outputs may use a first pattern to achieve subperception therapy at a location where paresthesia is separately provided, as well as at a second location such as the location for a DHS or an anatomical therapy.

Perfect sinusoidal outputs may be difficult to generate. For purposes of effecting a therapy at a "frequency" it should be understood that a spectral analysis of a signal will yield a power density function. A reasonable range of frequencies can serve as a bounding factor for understanding whether a therapy has been delivered at a desired frequency. For example, frequency delivered at 100 Hz may be taken to mean that at least a threshold percentage of total power delivered, or a threshold quantity of power, is delivered in a band of frequencies around 100 Hz such as a band from 95 Hz to 105 Hz. Illustrative threshold percentages may be, for example, 50% or more, 75% or more, or higher or lower. Such definitions may mean little to the practitioner but can be important to the designer who must convert the desired output into therapeutic parameters.

As illustration, a practitioner may determine through analysis of a given cell type that a frequency of 2 kHz to 20 kHz can be used to place a cell into a blocking state where it will remain generally refractory or non-responsive. A perfect sinusoid at 2 kHz should, theoretically, provide stimulus creating the blocking state, however, perfect sinusoids are difficult to create in implantable medical devices; the signal inherently has a beginning and an end, making it imperfect for at least this reason. To keep a minimum quantity of the power output above the purportedly effective frequency, various characteristics of a system output may need to be understood, as output filtering and the like can distort the desired waveshape. Therefore, the practitioner may determine to set about providing a therapy with at least 50% of delivered power at 2.2 to 2.4 kHz. The example here is prophetic; actual frequency boundaries for stimulus of a desired type, and available power ranges, may vary widely. To accommodate such analysis, a practitioner may be provided, via the CP, for example, spectral analysis tools to ensure that a planned therapy waveform possesses desirable frequency and power characteristics.

Once parameters link is identified at 420, therapy can be programmed. Therapy programming may be automated or manual and can take several forms. For example, a system may be designed to provide a physician a visualization of anatomical structures in a patient relative to implanted electrodes—or yet-to-be-implanted electrodes—and the physician identifies an anatomical location and designates a desired field level, from which the system determines an appropriate electrode combination to generate the desired field. An iterative process may follow in which the physician then reviews one or more proposed therapies that would generate the desired field, and could select one or several proposed therapies to test and then set about designating secondary therapies to mitigate against side effects of the proposed therapies.

Either prospectively, or as part of an iterative process, additional physiological parameters that affect stimulus outputs maybe determined as well. For example, certain physiology unique to the patient, such as muscle, fat, skeletal and other structures, can affect a therapy output and the field or current flow generated thereby. Areas of high or low impedance, tissue which responds in mirroring or shadowing manner to stimulus, structures which shield or block field incident upon a target structure may be accommodated with different spatial or temporal outputs.

For example, muscle tissue (lower impedance, relatively speaking) may shunt current away from a target, while bony structures (relatively higher impedance) may shield a target. More widely spaced electrodes may be used to address shielding concerns, for example, while narrower spacing may be chosen when current shunting is a concern.

In an alternative, the physician may use the CP to write the details of a given therapy pattern. This may include, for example, programming individual steps within a therapy pattern, and/or selecting functions to perform within a pattern. In another alternative, a physician may use a separate computer to write a therapy pattern and, transfer the therapy pattern using a transferrable memory (SD card or thumb drive for example), Bluetooth, WIFI or other communications to the CP or other in-system device such as the ETS, RC or IPG.

With a therapy pattern programmed at 440, therapy is tested at 460, and the outcome is then assessed at 480. Therapy testing 460 may include one or many subjects. Outcome assessment 480 may include direct observation of the therapy recipient, query and answer with a participant, and/or the use of imaging or measurement electronics to determine how particular anatomical structures respond. For example, evoked signals from neurons can be measured, or the strength of muscle contraction, extent of muscle relaxation, changes in other observables such as brain activity, tremor, memory, and cognition, etc. may be monitored and quantified. Subjective and objective determinations may be made on the outcomes, for example, using information gathered from questionnaires, physical observation, and direct measurement, or by other methods noted above.

Testing may rely on regression analysis to weight the received responses and, if a desired response is not received, further testing may occur on an iterative basis. Iterations may focus on the use of regression analysis to mathematically identify next steps. Alternatively, iterations may focus on assessing physiological tissues which were, or were not, affected in a predicted manner by application of therapy.

In an illustrative example, pain level is assessed (or wellness metric, activity metric, etc.) to identify a root cause by using a population study to identify correlations between spatial and temporal stimulation features and the desired therapeutic response. Features of patient-specific models of stimulation may be used (e.g., locations of specific field strengths, or effects of specific temporal stimulation methods). The assessment via a population study may include use of a regression analysis to separate out factors deemed most significant.

In an illustrative example, a pain level is assessed to identify a root cause by using a pre-clinical model of pain and measuring a pain level surrogate (e.g., imaging, local field potential characteristic, condition place preference, etc.) under several distinct spatio-temporal patterns of stimulation. In one embodiment, there are at least 5 or more distinct spatial components to the spatio-temporal pattern.

In an illustrative example, a tremor is assessed to identify a stimulation pattern that reduces the tremor by using at least the steps: first using a pattern output or approximation from a computational model, and second, refining the pattern using a search algorithm that includes measurement of a sensed physiologic signal and/or recording of subjective patient feedback.

In the following illustrative examples, a sensation may include any of pain, tingling, heat, cold, or substitution of a non-pain, non-heat, or non-cold, or other specific sensory input, when such ought to be felt. Also in the following illustrative examples, a cognitive abnormality may include a mood disorder, memory failure, or a state of distress or confusion not brought on by an external situation that, to the ordinary person, would bring on any such state.

Some examples make reference to population studies which may include review of chemical signals and/or genetics across a population to identify those of greater or lesser susceptibility to neurological disfunction and/or responsiveness to therapy. Such studies may include comparison of those patients who benefit from therapy to those who do not, as not all patients respond. For example given a large enough population and sufficient patient metrics, sensitivity analysis may be useful. Any suitable analysis may be used including, for example, genetic algorithms, gradient descent analysis, simplex analysis, binary searching, unidimensional and multidimensional assessment, and various sophisticated statistical techniques.

In several of the following illustrations, seeking out root cause may encompass fully identifying the specific source of pathological signals and the means whereby such signals propagate. In other examples, seeking out root cause may stop short of the identification of specific sources and means. In still other examples, the identification of root cause may take the form of identifying characteristics of a phenomenon to identify suitable ways to modulate the phenomenon, even if the underlying phenomenon remains unexplained at the deepest level.

In some examples, the patient condition of failure to respond to a biological signal may be broadly understood as incorporating a number of wellness metrics such as weight, chemical balance, blood analytes (cholesterol, triglycerides), thyroid or other hormonal activity, cardiac activity, overall physical activity, galvanic skin response, and involuntary or voluntary controls/responses such as reflex response, satiety, or voluntary control responses such as grip. In each instance, there is one or more "normal" physical outcomes which simply may not appear for a given patient.

In an illustrative example, a tremor is assessed to identify a root cause of degeneration, damage or malformation of a neurological pathway by performing a lesion study to identify an anatomic target for therapy to target.

In an illustrative example, a tremor is assessed to identify a root cause of degeneration, damage or malformation of a neurological pathway by performing an imaging study to identify an anatomic target for therapy to target.

In an illustrative example, a tremor is assessed to identify a root cause of degeneration, damage or malformation of a neurological pathway by capturing an intrinsic signal of a neurological structure to identify a therapy pattern to block, modulate, interrupt, augment or replace the intrinsic signal.

In an illustrative example, a tremor is assessed to identify a root cause of degeneration, damage or malformation of a neurological pathway by determining a cell or cell population level response to an electrical field or frequency, after determining a cell type for therapeutic assessment, to determine a needed electrical field, temporal or spatial pattern, or frequency for therapy.

In an illustrative example, a tremor is assessed to identify a root cause of degeneration, damage or malformation of a neurological pathway by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a tremor is assessed to identify a root cause of degeneration, damage or malformation of a neurological pathway by determining a therapy parameter effective for a first condition affected by a first neurological target, and translating the therapy parameter for use on a second condition and/or second neurological target.

In an illustrative example, a tremor is assessed to identify a root cause of degeneration, damage or malformation of a neurological pathway by studying an animal model, in vitro model, or in vivo model, to estimate a response for a corresponding or different human anatomical target.

In an illustrative example, a tremor is assessed to identify a root cause of degeneration, damage or malformation of a neurological pathway by using a population study to identify a difference between patients having the patient condition and persons who do not, and aligning the therapy parameters to a measurable difference between the patients and the persons.

In an illustrative example, a tremor is assessed to identify a root cause of plastic response to an internal bodily chemical imbalance or external chemical exposure by performing a lesion study to identify an anatomic target for therapy to target.

In an illustrative example, a tremor is assessed to identify a root cause of plastic response to an internal bodily chemical imbalance or external chemical exposure by performing an imaging study to identify an anatomic target for therapy to target.

In an illustrative example, a tremor is assessed to identify a root cause of plastic response to an internal bodily chemical imbalance or external chemical exposure by capturing an intrinsic signal of a neurological structure to identify a therapy pattern to block, modulate, interrupt, augment or replace the intrinsic signal.

In an illustrative example, a tremor is assessed to identify a root cause of plastic response to an internal bodily chemical imbalance or external chemical exposure by determining a cell or cell population level response to an electrical field or frequency, after determining a cell type for therapeutic assessment, to determine a needed electrical field, temporal or spatial pattern, or frequency for therapy.

In an illustrative example, a tremor is assessed to identify a root cause of plastic response to an internal bodily chemical imbalance or external chemical exposure by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a tremor is assessed to identify a root cause of plastic response to an internal bodily chemical imbalance or external chemical exposure by determining a therapy parameter effective for a first condition affected by a first neurological target, and translating the therapy parameter for use on a second condition and/or second neurological target.

In an illustrative example, a tremor is assessed to identify a root cause of plastic response to an internal bodily chemical imbalance or external chemical exposure by studying an animal model, in vitro model, or in vivo model, to estimate a response for a corresponding or different human anatomical target.

In an illustrative example, a tremor is assessed to identify a root cause of plastic response to an internal bodily chemical imbalance or external chemical exposure by using a population study to identify a difference between patients having the patient condition and persons who do not, and aligning the therapy parameters to a measurable difference between the patients and the persons.

In an illustrative example, a tremor is assessed to identify a root cause of existence of hyper-excitability or hypo-excitability of a neurological anatomy by performing a lesion study to identify an anatomic target for therapy to target.

In an illustrative example, a tremor is assessed to identify a root cause of existence of hyper-excitability or hypo-excitability of a neurological anatomy by performing an imaging study to identify an anatomic target for therapy to target.

In an illustrative example, a tremor is assessed to identify a root cause of existence of hyper-excitability or hypo-excitability of a neurological anatomy by capturing an intrinsic signal of a neurological structure to identify a therapy pattern to block, modulate, interrupt, augment or replace the intrinsic signal.

In an illustrative example, a tremor is assessed to identify a root cause of existence of hyper-excitability or hypo-excitability of a neurological anatomy by determining a cell or cell population level response to an electrical field or frequency, after determining a cell type for therapeutic assessment, to determine a needed electrical field, temporal or spatial pattern, or frequency for therapy.

In an illustrative example, a tremor is assessed to identify a root cause of existence of hyper-excitability or hypo-excitability of a neurological anatomy by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a tremor is assessed to identify a root cause of existence of hyper-excitability or hypo-excitability of a neurological anatomy by determining a therapy parameter effective for a first condition affected by a first neurological target, and translating the therapy parameter for use on a second condition and/or second neurological target.

In an illustrative example, a tremor is assessed to identify a root cause of existence of hyper-excitability or hypo-excitability of a neurological anatomy by studying an animal model, in vitro model, or in vivo model, to estimate a response for a corresponding or different human anatomical target.

In an illustrative example, a tremor is assessed to identify a root cause of existence of hyper-excitability or hypo-excitability of a neurological anatomy by using a population study to identify a difference between patients having the patient condition and persons who do not, and aligning the therapy parameters to a measurable difference between the patients and the persons.

In an illustrative example, a tremor is assessed to identify a root cause of overexcitation of a neural pathway by performing a lesion study to identify an anatomic target for therapy to target.

In an illustrative example, a tremor is assessed to identify a root cause of overexcitation of a neural pathway by performing an imaging study to identify an anatomic target for therapy to target.

In an illustrative example, a tremor is assessed to identify a root cause of overexcitation of a neural pathway by capturing an intrinsic signal of a neurological structure to identify a therapy pattern to block, modulate, interrupt, augment or replace the intrinsic signal.

In an illustrative example, a tremor is assessed to identify a root cause of overexcitation of a neural pathway by determining a cell or cell population level response to an electrical field or frequency, after determining a cell type for therapeutic assessment, to determine a needed electrical field, temporal or spatial pattern, or frequency for therapy.

In an illustrative example, a tremor is assessed to identify a root cause of overexcitation of a neural pathway by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a tremor is assessed to identify a root cause of overexcitation of a neural pathway by determining a therapy parameter effective for a first condition affected by a first neurological target, and translating the therapy parameter for use on a second condition and/or second neurological target.

In an illustrative example, a tremor is assessed to identify a root cause of overexcitation of a neural pathway by studying an animal model, in vitro model, or in vivo model, to estimate a response for a corresponding or different human anatomical target.

In an illustrative example, a tremor is assessed to identify a root cause of overexcitation of a neural pathway by using a population study to identify a difference between patients having the patient condition and persons who do not, and aligning the therapy parameters to a measurable difference between the patients and the persons.

In an illustrative example, a tremor is assessed to identify a root cause of pathological oscillation or synchrony of neurological structures by performing a lesion study to identify an anatomic target for therapy to target.

In an illustrative example, a tremor is assessed to identify a root cause of pathological oscillation or synchrony of neurological structures by performing an imaging study to identify an anatomic target for therapy to target.

In an illustrative example, a tremor is assessed to identify a root cause of pathological oscillation or synchrony of neurological structures by capturing an intrinsic signal of a neurological structure to identify a therapy pattern to block, modulate, interrupt, augment or replace the intrinsic signal.

In an illustrative example, a tremor is assessed to identify a root cause of pathological oscillation or synchrony of neurological structures by determining a cell or cell population level response to an electrical field or frequency, after determining a cell type for therapeutic assessment, to determine a needed electrical field, temporal or spatial pattern, or frequency for therapy.

In an illustrative example, a tremor is assessed to identify a root cause of pathological oscillation or synchrony of neurological structures by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a tremor is assessed to identify a root cause of pathological oscillation or synchrony of neurological structures by determining a therapy parameter effective for a first condition affected by a first neurological target, and translating the therapy parameter for use on a second condition and/or second neurological target.

In an illustrative example, a tremor is assessed to identify a root cause of pathological oscillation or synchrony of neurological structures by studying an animal model, in vitro model, or in vivo model, to estimate a response for a corresponding or different human anatomical target.

In an illustrative example, a tremor is assessed to identify a root cause of pathological oscillation or synchrony of neurological structures by using a population study to identify a difference between patients having the patient condition and persons who do not, and aligning the therapy parameters to a measurable difference between the patients and the persons.

In an illustrative example, a tremor is assessed to identify a root cause of incorrect or pathological generation, transmission or receipt of neurological, hormonal, visceral or glial signal by performing a lesion study to identify an anatomic target for therapy to target.

In an illustrative example, a tremor is assessed to identify a root cause of incorrect or pathological generation, transmission or receipt of neurological, hormonal, visceral or glial signal by performing an imaging study to identify an anatomic target for therapy to target.

In an illustrative example, a tremor is assessed to identify a root cause of incorrect or pathological generation, transmission or receipt of neurological, hormonal, visceral or glial signal by capturing an intrinsic signal of a neurological structure to identify a therapy pattern to block, modulate, interrupt, augment or replace the intrinsic signal.

In an illustrative example, a tremor is assessed to identify a root cause of incorrect or pathological generation, transmission or receipt of neurological, hormonal, visceral or glial signal by determining a cell or cell population level response to an electrical field or frequency, after determining a cell type for therapeutic assessment, to determine a needed electrical field, temporal or spatial pattern, or frequency for therapy.

In an illustrative example, a tremor is assessed to identify a root cause of incorrect or pathological generation, transmission or receipt of neurological, hormonal, visceral or glial signal by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a tremor is assessed to identify a root cause of incorrect or pathological generation, transmission or receipt of neurological, hormonal, visceral or glial signal by determining a therapy parameter effective for a first condition affected by a first neurological target, and translating the therapy parameter for use on a second condition and/or second neurological target.

In an illustrative example, a tremor is assessed to identify a root cause of incorrect or pathological generation, transmission or receipt of neurological, hormonal, visceral or glial signal by studying an animal model, in vitro model, or in vivo model, to estimate a response for a corresponding or different human anatomical target.

In an illustrative example, a tremor is assessed to identify a root cause of incorrect or pathological generation, transmission or receipt of neurological, hormonal, visceral or glial signal by using a population study to identify a difference between patients having the patient condition and persons who do not, and aligning the therapy parameters to a measurable difference between the patients and the persons.

In an illustrative example, a tremor is assessed to identify a root cause of presence or absence of a neurological, hormonal, visceral or glial signal to be blocked, modulated, supplemented or replaced by performing a lesion study to identify an anatomic target for therapy to target.

In an illustrative example, a tremor is assessed to identify a root cause of presence or absence of a neurological, hormonal, visceral or glial signal to be blocked, modulated, supplemented or replaced by performing an imaging study to identify an anatomic target for therapy to target.

In an illustrative example, a tremor is assessed to identify a root cause of presence or absence of a neurological, hormonal, visceral or glial signal to be blocked, modulated, supplemented or replaced by capturing an intrinsic signal of a neurological structure to identify a therapy pattern to block, modulate, interrupt, augment or replace the intrinsic signal.

In an illustrative example, a tremor is assessed to identify a root cause of presence or absence of a neurological, hormonal, visceral or glial signal to be blocked, modulated, supplemented or replaced by determining a cell or cell population level response to an electrical field or frequency, after determining a cell type for therapeutic assessment, to determine a needed electrical field, temporal or spatial pattern, or frequency for therapy.

In an illustrative example, a tremor is assessed to identify a root cause of presence or absence of a neurological, hormonal, visceral or glial signal to be blocked, modulated, supplemented or replaced by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a tremor is assessed to identify a root cause of presence or absence of a neurological, hormonal, visceral or glial signal to be blocked, modulated, supplemented or replaced by determining a therapy parameter effective for a first condition affected by a first neurological target, and translating the therapy parameter for use on a second condition and/or second neurological target.

In an illustrative example, a tremor is assessed to identify a root cause of presence or absence of a neurological, hormonal, visceral or glial signal to be blocked, modulated, supplemented or replaced by studying an animal model, in vitro model, or in vivo model, to estimate a response for a corresponding or different human anatomical target.

In an illustrative example, a tremor is assessed to identify a root cause of presence or absence of a neurological, hormonal, visceral or glial signal to be blocked, modulated, supplemented or replaced by using a population study to identify a difference between patients having the patient condition and persons who do not, and aligning the therapy parameters to a measurable difference between the patients and the persons.

In an illustrative example, a tremor is assessed to identify a root cause of presence or absence of sympathetic or parasympathetic nervous system responses by performing a lesion study to identify an anatomic target for therapy to target.

In an illustrative example, a tremor is assessed to identify a root cause of presence or absence of sympathetic or parasympathetic nervous system responses by performing an imaging study to identify an anatomic target for therapy to target.

In an illustrative example, a tremor is assessed to identify a root cause of presence or absence of sympathetic or parasympathetic nervous system responses by capturing an intrinsic signal of a neurological structure to identify a therapy pattern to block, modulate, interrupt, augment or replace the intrinsic signal.

In an illustrative example, a tremor is assessed to identify a root cause of presence or absence of sympathetic or parasympathetic nervous system responses by determining a cell or cell population level response to an electrical field or frequency, after determining a cell type for therapeutic assessment, to determine a needed electrical field, temporal or spatial pattern, or frequency for therapy.

In an illustrative example, a tremor is assessed to identify a root cause of presence or absence of sympathetic or parasympathetic nervous system responses by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a tremor is assessed to identify a root cause of presence or absence of sympathetic or parasympathetic nervous system responses by determining a therapy parameter effective for a first condition affected by a first neurological target, and translating the therapy parameter for use on a second condition and/or second neurological target.

In an illustrative example, a tremor is assessed to identify a root cause of presence or absence of sympathetic or parasympathetic nervous system responses by studying an animal model, in vitro model, or in vivo model, to estimate a response for a corresponding or different human anatomical target.

In an illustrative example, a tremor is assessed to identify a root cause of presence or absence of sympathetic or parasympathetic nervous system responses by using a population study to identify a difference between patients having the patient condition and persons who do not, and aligning the therapy parameters to a measurable difference between the patients and the persons.

In an illustrative example, a sensation is assessed to identify a root cause of degeneration, damage or malformation of a neurological pathway by performing a lesion study to identify an anatomic target for therapy to target.

In an illustrative example, a sensation is assessed to identify a root cause of degeneration, damage or malformation of a neurological pathway by performing an imaging study to identify an anatomic target for therapy to target.

In an illustrative example, a sensation is assessed to identify a root cause of degeneration, damage or malformation of a neurological pathway by capturing an intrinsic signal of a neurological structure to identify a therapy pattern to block, modulate, interrupt, augment or replace the intrinsic signal.

In an illustrative example, a sensation is assessed to identify a root cause of degeneration, damage or malformation of a neurological pathway by determining a cell or cell population level response to an electrical field or frequency, after determining a cell type for therapeutic assessment, to determine a needed electrical field, temporal or spatial pattern, or frequency for therapy.

In an illustrative example, a sensation is assessed to identify a root cause of degeneration, damage or malformation of a neurological pathway by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a sensation is assessed to identify a root cause of degeneration, damage or malformation of a neurological pathway by determining a therapy parameter effective for a first condition affected by a first neurological target, and translating the therapy parameter for use on a second condition and/or second neurological target.

In an illustrative example, a sensation is assessed to identify a root cause of degeneration, damage or malformation of a neurological pathway by studying an animal model, in vitro model, or in vivo model, to estimate a response for a corresponding or different human anatomical target.

In an illustrative example, a sensation is assessed to identify a root cause of degeneration, damage or malformation of a neurological pathway by using a population study to identify a difference between patients having the patient condition and persons who do not, and aligning the therapy parameters to a measurable difference between the patients and the persons.

In an illustrative example, a sensation is assessed to identify a root cause of plastic response to an internal bodily chemical imbalance or external chemical exposure by performing a lesion study to identify an anatomic target for therapy to target.

In an illustrative example, a sensation is assessed to identify a root cause of plastic response to an internal bodily chemical imbalance or external chemical exposure by performing an imaging study to identify an anatomic target for therapy to target.

In an illustrative example, a sensation is assessed to identify a root cause of plastic response to an internal bodily chemical imbalance or external chemical exposure by capturing an intrinsic signal of a neurological structure to identify a therapy pattern to block, modulate, interrupt, augment or replace the intrinsic signal.

In an illustrative example, a sensation is assessed to identify a root cause of plastic response to an internal bodily chemical imbalance or external chemical exposure by determining a cell or cell population level response to an electrical field or frequency, after determining a cell type for therapeutic assessment, to determine a needed electrical field, temporal or spatial pattern, or frequency for therapy.

In an illustrative example, a sensation is assessed to identify a root cause of plastic response to an internal bodily chemical imbalance or external chemical exposure by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a sensation is assessed to identify a root cause of plastic response to an internal bodily chemical imbalance or external chemical exposure by determining a therapy parameter effective for a first condition affected by a first neurological target, and translating the therapy parameter for use on a second condition and/or second neurological target.

In an illustrative example, a sensation is assessed to identify a root cause of plastic response to an internal bodily chemical imbalance or external chemical exposure by studying an animal model, in vitro model, or in vivo model, to estimate a response for a corresponding or different human anatomical target.

In an illustrative example, a sensation is assessed to identify a root cause of plastic response to an internal bodily chemical imbalance or external chemical exposure by using a population study to identify a difference between patients having the patient condition and persons who do not, and aligning the therapy parameters to a measurable difference between the patients and the persons.

In an illustrative example, a sensation is assessed to identify a root cause of existence of hyper-excitability or hypo-excitability of a neurological anatomy by performing a lesion study to identify an anatomic target for therapy to target.

In an illustrative example, a sensation is assessed to identify a root cause of existence of hyper-excitability or hypo-excitability of a neurological anatomy by performing an imaging study to identify an anatomic target for therapy to target.

In an illustrative example, a sensation is assessed to identify a root cause of existence of hyper-excitability or hypo-excitability of a neurological anatomy by capturing an intrinsic signal of a neurological structure to identify a therapy pattern to block, modulate, interrupt, augment or replace the intrinsic signal.

In an illustrative example, a sensation is assessed to identify a root cause of existence of hyper-excitability or hypo-excitability of a neurological anatomy by determining a cell or cell population level response to an electrical field or frequency, after determining a cell type for therapeutic assessment, to determine a needed electrical field, temporal or spatial pattern, or frequency for therapy.

In an illustrative example, a sensation is assessed to identify a root cause of existence of hyper-excitability or hypo-excitability of a neurological anatomy by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a sensation is assessed to identify a root cause of existence of hyper-excitability or hypo-excitability of a neurological anatomy by determining a therapy parameter effective for a first condition affected by a first neurological target, and translating the therapy parameter for use on a second condition and/or second neurological target.

In an illustrative example, a sensation is assessed to identify a root cause of existence of hyper-excitability or hypo-excitability of a neurological anatomy by studying an animal model, in vitro model, or in vivo model, to estimate a response for a corresponding or different human anatomical target.

In an illustrative example, a sensation is assessed to identify a root cause of existence of hyper-excitability or hypo-excitability of a neurological anatomy by using a population study to identify a difference between patients having the patient condition and persons who do not, and aligning the therapy parameters to a measurable difference between the patients and the persons.

In an illustrative example, a sensation is assessed to identify a root cause of overexcitation of a neural pathway by performing a lesion study to identify an anatomic target for therapy to target.

In an illustrative example, a sensation is assessed to identify a root cause of overexcitation of a neural pathway by performing an imaging study to identify an anatomic target for therapy to target.

In an illustrative example, a sensation is assessed to identify a root cause of overexcitation of a neural pathway by capturing an intrinsic signal of a neurological structure to identify a therapy pattern to block, modulate, interrupt, augment or replace the intrinsic signal.

In an illustrative example, a sensation is assessed to identify a root cause of overexcitation of a neural pathway by determining a cell or cell population level response to an electrical field or frequency, after determining a cell type for therapeutic assessment, to determine a needed electrical field, temporal or spatial pattern, or frequency for therapy.

In an illustrative example, a sensation is assessed to identify a root cause of overexcitation of a neural pathway by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a sensation is assessed to identify a root cause of overexcitation of a neural pathway by determining a therapy parameter effective for a first condition affected by a first neurological target, and translating the therapy parameter for use on a second condition and/or second neurological target.

In an illustrative example, a sensation is assessed to identify a root cause of overexcitation of a neural pathway by studying an animal model, in vitro model, or in vivo model, to estimate a response for a corresponding or different human anatomical target.

In an illustrative example, a sensation is assessed to identify a root cause of overexcitation of a neural pathway by using a population study to identify a difference between patients having the patient condition and persons who do not, and aligning the therapy parameters to a measurable difference between the patients and the persons.

In an illustrative example, a sensation is assessed to identify a root cause of pathological oscillation or synchrony of neurological structures by performing a lesion study to identify an anatomic target for therapy to target.

In an illustrative example, a sensation is assessed to identify a root cause of pathological oscillation or synchrony of neurological structures by performing an imaging study to identify an anatomic target for therapy to target.

In an illustrative example, a sensation is assessed to identify a root cause of pathological oscillation or synchrony of neurological structures by capturing an intrinsic signal of a neurological structure to identify a therapy pattern to block, modulate, interrupt, augment or replace the intrinsic signal.

In an illustrative example, a sensation is assessed to identify a root cause of pathological oscillation or synchrony of neurological structures by determining a cell or cell population level response to an electrical field or frequency, after determining a cell type for therapeutic assessment, to determine a needed electrical field, temporal or spatial pattern, or frequency for therapy.

In an illustrative example, a sensation is assessed to identify a root cause of pathological oscillation or synchrony of neurological structures by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a sensation is assessed to identify a root cause of pathological oscillation or synchrony of neurological structures by determining a therapy parameter effective for a first condition affected by a first neurological target, and translating the therapy parameter for use on a second condition and/or second neurological target.

In an illustrative example, a sensation is assessed to identify a root cause of pathological oscillation or synchrony of neurological structures by studying an animal model, in vitro model, or in vivo model, to estimate a response for a corresponding or different human anatomical target.

In an illustrative example, a sensation is assessed to identify a root cause of pathological oscillation or synchrony of neurological structures by using a population study to identify a difference between patients having the patient condition and persons who do not, and aligning the therapy parameters to a measurable difference between the patients and the persons.

In an illustrative example, a sensation is assessed to identify a root cause of incorrect or pathological generation, transmission or receipt of neurological, hormonal, visceral or glial signal by performing a lesion study to identify an anatomic target for therapy to target.

In an illustrative example, a sensation is assessed to identify a root cause of incorrect or pathological generation, transmission or receipt of neurological, hormonal, visceral or glial signal by performing an imaging study to identify an anatomic target for therapy to target.

In an illustrative example, a sensation is assessed to identify a root cause of incorrect or pathological generation, transmission or receipt of neurological, hormonal, visceral or glial signal by capturing an intrinsic signal of a neurological structure to identify a therapy pattern to block, modulate, interrupt, augment or replace the intrinsic signal.

In an illustrative example, a sensation is assessed to identify a root cause of incorrect or pathological generation, transmission or receipt of neurological, hormonal, visceral or glial signal by determining a cell or cell population level response to an electrical field or frequency, after determining a cell type for therapeutic assessment, to determine a needed electrical field, temporal or spatial pattern, or frequency for therapy.

In an illustrative example, a sensation is assessed to identify a root cause of incorrect or pathological generation, transmission or receipt of neurological, hormonal, visceral or glial signal by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a sensation is assessed to identify a root cause of incorrect or pathological generation, transmission or receipt of neurological, hormonal, visceral or glial signal by determining a therapy parameter effective for a first condition affected by a first neurological target, and translating the therapy parameter for use on a second condition and/or second neurological target.

In an illustrative example, a sensation is assessed to identify a root cause of incorrect or pathological generation, transmission or receipt of neurological, hormonal, visceral or glial signal by studying an animal model, in vitro model, or in vivo model, to estimate a response for a corresponding or different human anatomical target.

In an illustrative example, a sensation is assessed to identify a root cause of incorrect or pathological generation, transmission or receipt of neurological, hormonal, visceral or glial signal by using a population study to identify a difference between patients having the patient condition and persons who do not, and aligning the therapy parameters to a measurable difference between the patients and the persons.

In an illustrative example, a sensation is assessed to identify a root cause of presence or absence of a neurological, hormonal, visceral or glial signal to be blocked, modulated, supplemented or replaced by performing a lesion study to identify an anatomic target for therapy to target.

In an illustrative example, a sensation is assessed to identify a root cause of presence or absence of a neurological, hormonal, visceral or glial signal to be blocked, modulated, supplemented or replaced by performing an imaging study to identify an anatomic target for therapy to target.

In an illustrative example, a sensation is assessed to identify a root cause of presence or absence of a neurological, hormonal, visceral or glial signal to be blocked, modulated, supplemented or replaced by capturing an intrinsic signal of a neurological structure to identify a therapy pattern to block, modulate, interrupt, augment or replace the intrinsic signal.

In an illustrative example, a sensation is assessed to identify a root cause of presence or absence of a neurological, hormonal, visceral or glial signal to be blocked, modulated, supplemented or replaced by determining a cell or cell population level response to an electrical field or frequency, after determining a cell type for therapeutic assessment, to determine a needed electrical field, temporal or spatial pattern, or frequency for therapy.

In an illustrative example, a sensation is assessed to identify a root cause of presence or absence of a neurological, hormonal, visceral or glial signal to be blocked, modulated, supplemented or replaced by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a sensation is assessed to identify a root cause of presence or absence of a neurological, hormonal, visceral or glial signal to be blocked, modulated, supplemented or replaced by determining a therapy parameter effective for a first condition affected by a first neurological target, and translating the therapy parameter for use on a second condition and/or second neurological target.

In an illustrative example, a sensation is assessed to identify a root cause of presence or absence of a neurological, hormonal, visceral or glial signal to be blocked, modulated, supplemented or replaced by studying an animal model, in vitro model, or in vivo model, to estimate a response for a corresponding or different human anatomical target.

In an illustrative example, a sensation is assessed to identify a root cause of presence or absence of a neurological, hormonal, visceral or glial signal to be blocked, modulated, supplemented or replaced by using a population study to identify a difference between patients having the patient condition and persons who do not, and aligning the therapy parameters to a measurable difference between the patients and the persons.

In an illustrative example, a sensation is assessed to identify a root cause of presence or absence of sympathetic or parasympathetic nervous system responses by performing a lesion study to identify an anatomic target for therapy to target.

In an illustrative example, a sensation is assessed to identify a root cause of presence or absence of sympathetic or parasympathetic nervous system responses by performing an imaging study to identify an anatomic target for therapy to target.

In an illustrative example, a sensation is assessed to identify a root cause of presence or absence of sympathetic or parasympathetic nervous system responses by capturing an intrinsic signal of a neurological structure to identify a therapy pattern to block, modulate, interrupt, augment or replace the intrinsic signal.

In an illustrative example, a sensation is assessed to identify a root cause of presence or absence of sympathetic or parasympathetic nervous system responses by determining a cell or cell population level response to an electrical field or frequency, after determining a cell type for therapeutic assessment, to determine a needed electrical field, temporal or spatial pattern, or frequency for therapy.

In an illustrative example, a sensation is assessed to identify a root cause of presence or absence of sympathetic or parasympathetic nervous system responses by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a sensation is assessed to identify a root cause of presence or absence of sympathetic or parasympathetic nervous system responses by determining a therapy parameter effective for a first condition affected by a first neurological target, and translating the therapy parameter for use on a second condition and/or second neurological target.

In an illustrative example, a sensation is assessed to identify a root cause of presence or absence of sympathetic or parasympathetic nervous system responses by studying an animal model, in vitro model, or in vivo model, to estimate a response for a corresponding or different human anatomical target.

In an illustrative example, a sensation is assessed to identify a root cause of presence or absence of sympathetic or parasympathetic nervous system responses by using a population study to identify a difference between patients having the patient condition and persons who do not, and aligning the therapy parameters to a measurable difference between the patients and the persons.

In an illustrative example, a weakness is assessed to identify a root cause of degeneration, damage or malformation of a neurological pathway by performing a lesion study to identify an anatomic target for therapy to target.

In an illustrative example, a weakness is assessed to identify a root cause of degeneration, damage or malformation of a neurological pathway by performing an imaging study to identify an anatomic target for therapy to target.

In an illustrative example, a weakness is assessed to identify a root cause of degeneration, damage or malformation of a neurological pathway by capturing an intrinsic signal of a neurological structure to identify a therapy pattern to block, modulate, interrupt, augment or replace the intrinsic signal.

In an illustrative example, a weakness is assessed to identify a root cause of degeneration, damage or malformation of a neurological pathway by determining a cell or cell population level response to an electrical field or frequency, after determining a cell type for therapeutic assessment, to determine a needed electrical field, temporal or spatial pattern, or frequency for therapy.

In an illustrative example, a weakness is assessed to identify a root cause of degeneration, damage or malformation of a neurological pathway by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a weakness is assessed to identify a root cause of degeneration, damage or malformation of a neurological pathway by determining a therapy parameter effective for a first condition affected by a first neurological target, and translating the therapy parameter for use on a second condition and/or second neurological target.

In an illustrative example, a weakness is assessed to identify a root cause of degeneration, damage or malformation of a neurological pathway by studying an animal model, in vitro model, or in vivo model, to estimate a response for a corresponding or different human anatomical target.

In an illustrative example, a weakness is assessed to identify a root cause of degeneration, damage or malformation of a neurological pathway by using a population study to identify a difference between patients having the patient condition and persons who do not, and aligning the therapy parameters to a measurable difference between the patients and the persons.

In an illustrative example, a weakness is assessed to identify a root cause of plastic response to an internal bodily chemical imbalance or external chemical exposure by performing a lesion study to identify an anatomic target for therapy to target.

In an illustrative example, a weakness is assessed to identify a root cause of plastic response to an internal bodily chemical imbalance or external chemical exposure by performing an imaging study to identify an anatomic target for therapy to target.

In an illustrative example, a weakness is assessed to identify a root cause of plastic response to an internal bodily chemical imbalance or external chemical exposure by capturing an intrinsic signal of a neurological structure to identify a therapy pattern to block, modulate, interrupt, augment or replace the intrinsic signal.

In an illustrative example, a weakness is assessed to identify a root cause of plastic response to an internal bodily chemical imbalance or external chemical exposure by determining a cell or cell population level response to an electrical field or frequency, after determining a cell type for therapeutic assessment, to determine a needed electrical field, temporal or spatial pattern, or frequency for therapy.

In an illustrative example, a weakness is assessed to identify a root cause of plastic response to an internal bodily chemical imbalance or external chemical exposure by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a weakness is assessed to identify a root cause of plastic response to an internal bodily chemical imbalance or external chemical exposure by determining a therapy parameter effective for a first condition affected by a first neurological target, and translating the therapy parameter for use on a second condition and/or second neurological target.

In an illustrative example, a weakness is assessed to identify a root cause of plastic response to an internal bodily chemical imbalance or external chemical exposure by studying an animal model, in vitro model, or in vivo model, to estimate a response for a corresponding or different human anatomical target.

In an illustrative example, a weakness is assessed to identify a root cause of plastic response to an internal bodily chemical imbalance or external chemical exposure by using a population study to identify a difference between patients having the patient condition and persons who do not, and aligning the therapy parameters to a measurable difference between the patients and the persons.

In an illustrative example, a weakness is assessed to identify a root cause of existence of hyper-excitability or hypo-excitability of a neurological anatomy by performing a lesion study to identify an anatomic target for therapy to target.

In an illustrative example, a weakness is assessed to identify a root cause of existence of hyper-excitability or hypo-excitability of a neurological anatomy by performing an imaging study to identify an anatomic target for therapy to target.

In an illustrative example, a weakness is assessed to identify a root cause of existence of hyper-excitability or hypo-excitability of a neurological anatomy by capturing an intrinsic signal of a neurological structure to identify a therapy pattern to block, modulate, interrupt, augment or replace the intrinsic signal.

In an illustrative example, a weakness is assessed to identify a root cause of existence of hyper-excitability or hypo-excitability of a neurological anatomy by determining a cell or cell population level response to an electrical field or frequency, after determining a cell type for therapeutic assessment, to determine a needed electrical field, temporal or spatial pattern, or frequency for therapy.

In an illustrative example, a weakness is assessed to identify a root cause of existence of hyper-excitability or hypo-excitability of a neurological anatomy by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a weakness is assessed to identify a root cause of existence of hyper-excitability or hypo-excitability of a neurological anatomy by determining a therapy parameter effective for a first condition affected by a first neurological target, and translating the therapy parameter for use on a second condition and/or second neurological target.

In an illustrative example, a weakness is assessed to identify a root cause of existence of hyper-excitability or hypo-excitability of a neurological anatomy by studying an animal model, in vitro model, or in vivo model, to estimate a response for a corresponding or different human anatomical target.

In an illustrative example, a weakness is assessed to identify a root cause of existence of hyper-excitability or hypo-excitability of a neurological anatomy by using a population study to identify a difference between patients having the patient condition and persons who do not, and aligning the therapy parameters to a measurable difference between the patients and the persons.

In an illustrative example, a weakness is assessed to identify a root cause of overexcitation of a neural pathway by performing a lesion study to identify an anatomic target for therapy to target.

In an illustrative example, a weakness is assessed to identify a root cause of overexcitation of a neural pathway by performing an imaging study to identify an anatomic target for therapy to target.

In an illustrative example, a weakness is assessed to identify a root cause of overexcitation of a neural pathway by capturing an intrinsic signal of a neurological structure to identify a therapy pattern to block, modulate, interrupt, augment or replace the intrinsic signal.

In an illustrative example, a weakness is assessed to identify a root cause of overexcitation of a neural pathway by determining a cell or cell population level response to an electrical field or frequency, after determining a cell type for therapeutic assessment, to determine a needed electrical field, temporal or spatial pattern, or frequency for therapy.

In an illustrative example, a weakness is assessed to identify a root cause of overexcitation of a neural pathway by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a weakness is assessed to identify a root cause of overexcitation of a neural pathway by determining a therapy parameter effective for a first condition affected by a first neurological target, and translating the therapy parameter for use on a second condition and/or second neurological target.

In an illustrative example, a weakness is assessed to identify a root cause of overexcitation of a neural pathway by studying an animal model, in vitro model, or in vivo model, to estimate a response for a corresponding or different human anatomical target.

In an illustrative example, a weakness is assessed to identify a root cause of overexcitation of a neural pathway by using a population study to identify a difference between patients having the patient condition and persons who do not, and aligning the therapy parameters to a measurable difference between the patients and the persons.

In an illustrative example, a weakness is assessed to identify a root cause of pathological oscillation or synchrony of neurological structures by performing a lesion study to identify an anatomic target for therapy to target.

In an illustrative example, a weakness is assessed to identify a root cause of pathological oscillation or synchrony of neurological structures by performing an imaging study to identify an anatomic target for therapy to target.

In an illustrative example, a weakness is assessed to identify a root cause of pathological oscillation or synchrony of neurological structures by capturing an intrinsic signal of a neurological structure to identify a therapy pattern to block, modulate, interrupt, augment or replace the intrinsic signal.

In an illustrative example, a weakness is assessed to identify a root cause of pathological oscillation or synchrony of neurological structures by determining a cell or cell population level response to an electrical field or frequency, after determining a cell type for therapeutic assessment, to determine a needed electrical field, temporal or spatial pattern, or frequency for therapy.

In an illustrative example, a weakness is assessed to identify a root cause of pathological oscillation or synchrony of neurological structures by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a weakness is assessed to identify a root cause of pathological oscillation or synchrony of neurological structures by determining a therapy parameter effective for a first condition affected by a first neurological target, and translating the therapy parameter for use on a second condition and/or second neurological target.

In an illustrative example, a weakness is assessed to identify a root cause of pathological oscillation or synchrony of neurological structures by studying an animal model, in vitro model, or in vivo model, to estimate a response for a corresponding or different human anatomical target.

In an illustrative example, a weakness is assessed to identify a root cause of pathological oscillation or synchrony of neurological structures by using a population study to identify a difference between patients having the patient condition and persons who do not, and aligning the therapy parameters to a measurable difference between the patients and the persons.

In an illustrative example, a weakness is assessed to identify a root cause of incorrect or pathological generation, transmission or receipt of neurological, hormonal, visceral or glial signal by performing a lesion study to identify an anatomic target for therapy to target.

In an illustrative example, a weakness is assessed to identify a root cause of incorrect or pathological generation, transmission or receipt of neurological, hormonal, visceral or glial signal by performing an imaging study to identify an anatomic target for therapy to target.

In an illustrative example, a weakness is assessed to identify a root cause of incorrect or pathological generation, transmission or receipt of neurological, hormonal, visceral or glial signal by capturing an intrinsic signal of a neurological structure to identify a therapy pattern to block, modulate, interrupt, augment or replace the intrinsic signal.

In an illustrative example, a weakness is assessed to identify a root cause of incorrect or pathological generation, transmission or receipt of neurological, hormonal, visceral or glial signal by determining a cell or cell population level response to an electrical field or frequency, after determining a cell type for therapeutic assessment, to determine a needed electrical field, temporal or spatial pattern, or frequency for therapy.

In an illustrative example, a weakness is assessed to identify a root cause of incorrect or pathological generation, transmission or receipt of neurological, hormonal, visceral or glial signal by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a weakness is assessed to identify a root cause of incorrect or pathological generation, transmission or receipt of neurological, hormonal, visceral or glial signal by determining a therapy parameter effective for a first condition affected by a first neurological target, and translating the therapy parameter for use on a second condition and/or second neurological target.

In an illustrative example, a weakness is assessed to identify a root cause of incorrect or pathological generation, transmission or receipt of neurological, hormonal, visceral or glial signal by studying an animal model, in vitro model, or in vivo model, to estimate a response for a corresponding or different human anatomical target.

In an illustrative example, a weakness is assessed to identify a root cause of incorrect or pathological generation, transmission or receipt of neurological, hormonal, visceral or glial signal by using a population study to identify a difference between patients having the patient condition and persons who do not, and aligning the therapy parameters to a measurable difference between the patients and the persons.

In an illustrative example, a weakness is assessed to identify a root cause of presence or absence of a neurological, hormonal, visceral or glial signal to be blocked, modulated, supplemented or replaced by performing a lesion study to identify an anatomic target for therapy to target.

In an illustrative example, a weakness is assessed to identify a root cause of presence or absence of a neurological, hormonal, visceral or glial signal to be blocked, modulated, supplemented or replaced by performing an imaging study to identify an anatomic target for therapy to target.

In an illustrative example, a weakness is assessed to identify a root cause of presence or absence of a neurological, hormonal, visceral or glial signal to be blocked, modulated, supplemented or replaced by capturing an intrinsic signal of a neurological structure to identify a therapy pattern to block, modulate, interrupt, augment or replace the intrinsic signal.

In an illustrative example, a weakness is assessed to identify a root cause of presence or absence of a neurological, hormonal, visceral or glial signal to be blocked, modulated, supplemented or replaced by determining a cell or cell population level response to an electrical field or frequency, after determining a cell type for therapeutic assessment, to determine a needed electrical field, temporal or spatial pattern, or frequency for therapy.

In an illustrative example, a weakness is assessed to identify a root cause of presence or absence of a neurological, hormonal, visceral or glial signal to be blocked, modulated, supplemented or replaced by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a weakness is assessed to identify a root cause of presence or absence of a neurological, hormonal, visceral or glial signal to be blocked, modulated, supplemented or replaced by determining a therapy parameter effective for a first condition affected by a first neurological target, and translating the therapy parameter for use on a second condition and/or second neurological target.

In an illustrative example, a weakness is assessed to identify a root cause of presence or absence of a neurological, hormonal, visceral or glial signal to be blocked, modulated, supplemented or replaced by studying an animal model, in vitro model, or in vivo model, to estimate a response for a corresponding or different human anatomical target.

In an illustrative example, a weakness is assessed to identify a root cause of presence or absence of a neurological, hormonal, visceral or glial signal to be blocked, modulated, supplemented or replaced by using a population study to identify a difference between patients having the patient condition and persons who do not, and aligning the therapy parameters to a measurable difference between the patients and the persons.

In an illustrative example, a weakness is assessed to identify a root cause of presence or absence of sympathetic or parasympathetic nervous system responses by performing a lesion study to identify an anatomic target for therapy to target.

In an illustrative example, a weakness is assessed to identify a root cause of presence or absence of sympathetic or parasympathetic nervous system responses by performing an imaging study to identify an anatomic target for therapy to target.

In an illustrative example, a weakness is assessed to identify a root cause of presence or absence of sympathetic or parasympathetic nervous system responses by capturing an intrinsic signal of a neurological structure to identify a therapy pattern to block, modulate, interrupt, augment or replace the intrinsic signal.

In an illustrative example, a weakness is assessed to identify a root cause of presence or absence of sympathetic or parasympathetic nervous system responses by determining a cell or cell population level response to an electrical field or frequency, after determining a cell type for therapeutic assessment, to determine a needed electrical field, temporal or spatial pattern, or frequency for therapy.

In an illustrative example, a weakness is assessed to identify a root cause of presence or absence of sympathetic or parasympathetic nervous system responses by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a weakness is assessed to identify a root cause of presence or absence of sympathetic or parasympathetic nervous system responses by determining a therapy parameter effective for a first condition affected by a first neurological target, and translating the therapy parameter for use on a second condition and/or second neurological target.

In an illustrative example, a weakness is assessed to identify a root cause of presence or absence of sympathetic or parasympathetic nervous system responses by studying an animal model, in vitro model, or in vivo model, to estimate a response for a corresponding or different human anatomical target.

In an illustrative example, a weakness is assessed to identify a root cause of presence or absence of sympathetic or parasympathetic nervous system responses by using a population study to identify a difference between patients having the patient condition and persons who do not, and aligning the therapy parameters to a measurable difference between the patients and the persons.

In an illustrative example, a failure to respond to a biological signal is assessed to identify a root cause of degeneration, damage or malformation of a neurological pathway by performing a lesion study to identify an anatomic target for therapy to target.

In an illustrative example, a failure to respond to a biological signal is assessed to identify a root cause of degeneration, damage or malformation of a neurological pathway by performing an imaging study to identify an anatomic target for therapy to target.

In an illustrative example, a failure to respond to a biological signal is assessed to identify a root cause of degeneration, damage or malformation of a neurological pathway by capturing an intrinsic signal of a neurological structure to identify a therapy pattern to block, modulate, interrupt, augment or replace the intrinsic signal.

In an illustrative example, a failure to respond to a biological signal is assessed to identify a root cause of degeneration, damage or malformation of a neurological pathway by determining a cell or cell population level response to an electrical field or frequency, after determining a cell type for therapeutic assessment, to determine a needed electrical field, temporal or spatial pattern, or frequency for therapy.

In an illustrative example, a failure to respond to a biological signal is assessed to identify a root cause of degeneration, damage or malformation of a neurological pathway by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a failure to respond to a biological signal is assessed to identify a root cause of degeneration, damage or malformation of a neurological pathway by determining a therapy parameter effective for a first condition affected by a first neurological target, and translating the therapy parameter for use on a second condition and/or second neurological target.

In an illustrative example, a failure to respond to a biological signal is assessed to identify a root cause of degeneration, damage or malformation of a neurological pathway by studying an animal model, in vitro model, or in vivo model, to estimate a response for a corresponding or different human anatomical target.

In an illustrative example, a failure to respond to a biological signal is assessed to identify a root cause of degeneration, damage or malformation of a neurological pathway by using a population study to identify a difference between patients having the patient condition and persons who do not, and aligning the therapy parameters to a measurable difference between the patients and the persons.

In an illustrative example, a failure to respond to a biological signal is assessed to identify a root cause of plastic response to an internal bodily chemical imbalance or external chemical exposure by performing a lesion study to identify an anatomic target for therapy to target.

In an illustrative example, a failure to respond to a biological signal is assessed to identify a root cause of plastic response to an internal bodily chemical imbalance or external chemical exposure by performing an imaging study to identify an anatomic target for therapy to target.

In an illustrative example, a failure to respond to a biological signal is assessed to identify a root cause of plastic response to an internal bodily chemical imbalance or external chemical exposure by capturing an intrinsic signal of a neurological structure to identify a therapy pattern to block, modulate, interrupt, augment or replace the intrinsic signal.

In an illustrative example, a failure to respond to a biological signal is assessed to identify a root cause of plastic response to an internal bodily chemical imbalance or external chemical exposure by determining a cell or cell population level response to an electrical field or frequency, after determining a cell type for therapeutic assessment, to determine a needed electrical field, temporal or spatial pattern, or frequency for therapy.

In an illustrative example, a failure to respond to a biological signal is assessed to identify a root cause of plastic response to an internal bodily chemical imbalance or external chemical exposure by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a failure to respond to a biological signal is assessed to identify a root cause of plastic response to an internal bodily chemical imbalance or external chemical exposure by determining a therapy parameter effective for a first condition affected by a first neurological target, and translating the therapy parameter for use on a second condition and/or second neurological target.

In an illustrative example, a failure to respond to a biological signal is assessed to identify a root cause of plastic response to an internal bodily chemical imbalance or external chemical exposure by studying an animal model, in vitro model, or in vivo model, to estimate a response for a corresponding or different human anatomical target.

In an illustrative example, a failure to respond to a biological signal is assessed to identify a root cause of plastic response to an internal bodily chemical imbalance or external chemical exposure by using a population study to identify a difference between patients having the patient condition and persons who do not, and aligning the therapy parameters to a measurable difference between the patients and the persons.

In an illustrative example, a failure to respond to a biological signal is assessed to identify a root cause of existence of hyper-excitability or hypo-excitability of a neurological anatomy by performing a lesion study to identify an anatomic target for therapy to target.

In an illustrative example, a failure to respond to a biological signal is assessed to identify a root cause of existence of hyper-excitability or hypo-excitability of a neurological anatomy by performing an imaging study to identify an anatomic target for therapy to target.

In an illustrative example, a failure to respond to a biological signal is assessed to identify a root cause of existence of hyper-excitability or hypo-excitability of a neurological anatomy by capturing an intrinsic signal of a neurological structure to identify a therapy pattern to block, modulate, interrupt, augment or replace the intrinsic signal.

In an illustrative example, a failure to respond to a biological signal is assessed to identify a root cause of existence of hyper-excitability or hypo-excitability of a neurological anatomy by determining a cell or cell population level response to an electrical field or frequency, after determining a cell type for therapeutic assessment, to determine a needed electrical field, temporal or spatial pattern, or frequency for therapy.

In an illustrative example, a failure to respond to a biological signal is assessed to identify a root cause of existence of hyper-excitability or hypo-excitability of a neurological anatomy by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a failure to respond to a biological signal is assessed to identify a root cause of existence of hyper-excitability or hypo-excitability of a neurological anatomy by determining a therapy parameter effective for a first condition affected by a first neurological target, and translating the therapy parameter for use on a second condition and/or second neurological target.

In an illustrative example, a failure to respond to a biological signal is assessed to identify a root cause of existence of hyper-excitability or hypo-excitability of a neurological anatomy by studying an animal model, in vitro model, or in vivo model, to estimate a response for a corresponding or different human anatomical target.

In an illustrative example, a failure to respond to a biological signal is assessed to identify a root cause of existence of hyper-excitability or hypo-excitability of a neurological anatomy by using a population study to identify a difference between patients having the patient condition and persons who do not, and aligning the therapy parameters to a measurable difference between the patients and the persons.

In an illustrative example, a failure to respond to a biological signal is assessed to identify a root cause of overexcitation of a neural pathway by performing a lesion study to identify an anatomic target for therapy to target.

In an illustrative example, a failure to respond to a biological signal is assessed to identify a root cause of overexcitation of a neural pathway by performing an imaging study to identify an anatomic target for therapy to target.

In an illustrative example, a failure to respond to a biological signal is assessed to identify a root cause of overexcitation of a neural pathway by capturing an intrinsic signal of a neurological structure to identify a therapy pattern to block, modulate, interrupt, augment or replace the intrinsic signal.

In an illustrative example, a failure to respond to a biological signal is assessed to identify a root cause of overexcitation of a neural pathway by determining a cell or cell population level response to an electrical field or frequency, after determining a cell type for therapeutic assessment, to determine a needed electrical field, temporal or spatial pattern, or frequency for therapy.

In an illustrative example, a failure to respond to a biological signal is assessed to identify a root cause of overexcitation of a neural pathway by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a failure to respond to a biological signal is assessed to identify a root cause of overexcitation of a neural pathway by determining a therapy parameter effective for a first condition affected by a first neurological target, and translating the therapy parameter for use on a second condition and/or second neurological target.

In an illustrative example, a failure to respond to a biological signal is assessed to identify a root cause of overexcitation of a neural pathway by studying an animal model, in vitro model, or in vivo model, to estimate a response for a corresponding or different human anatomical target.

In an illustrative example, a failure to respond to a biological signal is assessed to identify a root cause of overexcitation of a neural pathway by using a population study to identify a difference between patients having the patient condition and persons who do not, and aligning the therapy parameters to a measurable difference between the patients and the persons.

In an illustrative example, a failure to respond to a biological signal is assessed to identify a root cause of pathological oscillation or synchrony of neurological structures by performing a lesion study to identify an anatomic target for therapy to target.

In an illustrative example, a failure to respond to a biological signal is assessed to identify a root cause of pathological oscillation or synchrony of neurological structures by performing an imaging study to identify an anatomic target for therapy to target.

In an illustrative example, a failure to respond to a biological signal is assessed to identify a root cause of pathological oscillation or synchrony of neurological structures by capturing an intrinsic signal of a neurological structure to identify a therapy pattern to block, modulate, interrupt, augment or replace the intrinsic signal.

In an illustrative example, a failure to respond to a biological signal is assessed to identify a root cause of pathological oscillation or synchrony of neurological structures by determining a cell or cell population level response to an electrical field or frequency, after determining a cell type for therapeutic assessment, to determine a needed electrical field, temporal or spatial pattern, or frequency for therapy.

In an illustrative example, a failure to respond to a biological signal is assessed to identify a root cause of pathological oscillation or synchrony of neurological structures by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a failure to respond to a biological signal is assessed to identify a root cause of pathological oscillation or synchrony of neurological structures by determining a therapy parameter effective for a first condition affected by a first neurological target, and translating the therapy parameter for use on a second condition and/or second neurological target.

In an illustrative example, a failure to respond to a biological signal is assessed to identify a root cause of pathological oscillation or synchrony of neurological structures by studying an animal model, in vitro model, or in vivo model, to estimate a response for a corresponding or different human anatomical target.

In an illustrative example, a failure to respond to a biological signal is assessed to identify a root cause of pathological oscillation or synchrony of neurological structures by using a population study to identify a difference between patients having the patient condition and persons who do not, and aligning the therapy parameters to a measurable difference between the patients and the persons.

In an illustrative example, a failure to respond to a biological signal is assessed to identify a root cause of incorrect or pathological generation, transmission or receipt of neurological, hormonal, visceral or glial signal by performing a lesion study to identify an anatomic target for therapy to target.

In an illustrative example, a failure to respond to a biological signal is assessed to identify a root cause of incorrect or pathological generation, transmission or receipt of neurological, hormonal, visceral or glial signal by performing an imaging study to identify an anatomic target for therapy to target.

In an illustrative example, a failure to respond to a biological signal is assessed to identify a root cause of incorrect or pathological generation, transmission or receipt of neurological, hormonal, visceral or glial signal by capturing an intrinsic signal of a neurological structure to identify a therapy pattern to block, modulate, interrupt, augment or replace the intrinsic signal.

In an illustrative example, a failure to respond to a biological signal is assessed to identify a root cause of incorrect or pathological generation, transmission or receipt of neurological, hormonal, visceral or glial signal by determining a cell or cell population level response to an electrical field or frequency, after determining a cell type for therapeutic assessment, to determine a needed electrical field, temporal or spatial pattern, or frequency for therapy.

In an illustrative example, a failure to respond to a biological signal is assessed to identify a root cause of incorrect or pathological generation, transmission or receipt of neurological, hormonal, visceral or glial signal by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a failure to respond to a biological signal is assessed to identify a root cause of incorrect or pathological generation, transmission or receipt of neurological, hormonal, visceral or glial signal by determining a therapy parameter effective for a first condition affected by a first neurological target, and translating the therapy parameter for use on a second condition and/or second neurological target.

In an illustrative example, a failure to respond to a biological signal is assessed to identify a root cause of incorrect or pathological generation, transmission or receipt of neurological, hormonal, visceral or glial signal by studying an animal model, in vitro model, or in vivo model, to estimate a response for a corresponding or different human anatomical target.

In an illustrative example, a failure to respond to a biological signal is assessed to identify a root cause of incorrect or pathological generation, transmission or receipt of neurological, hormonal, visceral or glial signal by using a population study to identify a difference between patients having the patient condition and persons who do not, and aligning the therapy parameters to a measurable difference between the patients and the persons.

In an illustrative example, a failure to respond to a biological signal is assessed to identify a root cause of presence or absence of a neurological, hormonal, visceral or glial signal to be blocked, modulated, supplemented or replaced by performing a lesion study to identify an anatomic target for therapy to target.

In an illustrative example, a failure to respond to a biological signal is assessed to identify a root cause of presence or absence of a neurological, hormonal, visceral or glial signal to be blocked, modulated, supplemented or replaced by performing an imaging study to identify an anatomic target for therapy to target.

In an illustrative example, a failure to respond to a biological signal is assessed to identify a root cause of presence or absence of a neurological, hormonal, visceral or glial signal to be blocked, modulated, supplemented or replaced by capturing an intrinsic signal of a neurological structure to identify a therapy pattern to block, modulate, interrupt, augment or replace the intrinsic signal.

In an illustrative example, a failure to respond to a biological signal is assessed to identify a root cause of presence or absence of a neurological, hormonal, visceral or glial signal to be blocked, modulated, supplemented or replaced by determining a cell or cell population level response to an electrical field or frequency, after determining a cell type for therapeutic assessment, to determine a needed electrical field, temporal or spatial pattern, or frequency for therapy.

In an illustrative example, a failure to respond to a biological signal is assessed to identify a root cause of presence or absence of a neurological, hormonal, visceral or glial signal to be blocked, modulated, supplemented or replaced by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a failure to respond to a biological signal is assessed to identify a root cause of presence or absence of a neurological, hormonal, visceral or glial signal to be blocked, modulated, supplemented or replaced by determining a therapy parameter effective for a first condition affected by a first neurological target, and translating the therapy parameter for use on a second condition and/or second neurological target.

In an illustrative example, a failure to respond to a biological signal is assessed to identify a root cause of presence or absence of a neurological, hormonal, visceral or glial signal to be blocked, modulated, supplemented or replaced by studying an animal model, in vitro model, or in vivo model, to estimate a response for a corresponding or different human anatomical target.

In an illustrative example, a failure to respond to a biological signal is assessed to identify a root cause of presence or absence of a neurological, hormonal, visceral or glial signal to be blocked, modulated, supplemented or replaced by using a population study to identify a difference between patients having the patient condition and persons who do not, and aligning the therapy parameters to a measurable difference between the patients and the persons.

In an illustrative example, a failure to respond to a biological signal is assessed to identify a root cause of presence or absence of sympathetic or parasympathetic nervous system responses by performing a lesion study to identify an anatomic target for therapy to target.

In an illustrative example, a failure to respond to a biological signal is assessed to identify a root cause of presence or absence of sympathetic or parasympathetic nervous system responses by performing an imaging study to identify an anatomic target for therapy to target.

In an illustrative example, a failure to respond to a biological signal is assessed to identify a root cause of presence or absence of sympathetic or parasympathetic nervous system responses by capturing an intrinsic signal of a neurological structure to identify a therapy pattern to block, modulate, interrupt, augment or replace the intrinsic signal.

In an illustrative example, a failure to respond to a biological signal is assessed to identify a root cause of presence or absence of sympathetic or parasympathetic nervous system responses by determining a cell or cell population level response to an electrical field or frequency, after determining a cell type for therapeutic assessment, to determine a needed electrical field, temporal or spatial pattern, or frequency for therapy.

In an illustrative example, a failure to respond to a biological signal is assessed to identify a root cause of presence or absence of sympathetic or parasympathetic nervous system responses by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a failure to respond to a biological signal is assessed to identify a root cause of presence or absence of sympathetic or parasympathetic nervous system responses by determining a therapy parameter effective for a first condition affected by a first neurological target, and translating the therapy parameter for use on a second condition and/or second neurological target.

In an illustrative example, a failure to respond to a biological signal is assessed to identify a root cause of presence or absence of sympathetic or parasympathetic nervous system responses by studying an animal model, in vitro model, or in vivo model, to estimate a response for a corresponding or different human anatomical target.

In an illustrative example, a failure to respond to a biological signal is assessed to identify a root cause of presence or absence of sympathetic or parasympathetic nervous system responses by using a population study to identify a difference between patients having the patient condition and persons who do not, and aligning the therapy parameters to a measurable difference between the patients and the persons.

In an illustrative example, a cognitive abnormality is assessed to identify a root cause of degeneration, damage or malformation of a neurological pathway by performing a lesion study to identify an anatomic target for therapy to target.

In an illustrative example, a cognitive abnormality is assessed to identify a root cause of degeneration, damage or malformation of a neurological pathway by performing an imaging study to identify an anatomic target for therapy to target.

In an illustrative example, a cognitive abnormality is assessed to identify a root cause of degeneration, damage or malformation of a neurological pathway by capturing an intrinsic signal of a neurological structure to identify a therapy pattern to block, modulate, interrupt, augment or replace the intrinsic signal.

In an illustrative example, a cognitive abnormality is assessed to identify a root cause of degeneration, damage or malformation of a neurological pathway by determining a cell or cell population level response to an electrical field or frequency, after determining a cell type for therapeutic assessment, to determine a needed electrical field, temporal or spatial pattern, or frequency for therapy.

In an illustrative example, a cognitive abnormality is assessed to identify a root cause of degeneration, damage or malformation of a neurological pathway by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a cognitive abnormality is assessed to identify a root cause of degeneration, damage or malformation of a neurological pathway by determining a therapy parameter effective for a first condition affected by a first neurological target, and translating the therapy parameter for use on a second condition and/or second neurological target.

In an illustrative example, a cognitive abnormality is assessed to identify a root cause of degeneration, damage or malformation of a neurological pathway by studying an animal model, in vitro model, or in vivo model, to estimate a response for a corresponding or different human anatomical target.

In an illustrative example, a cognitive abnormality is assessed to identify a root cause of degeneration, damage or malformation of a neurological pathway by using a population study to identify a difference between patients having the patient condition and persons who do not, and aligning the therapy parameters to a measurable difference between the patients and the persons.

In an illustrative example, a cognitive abnormality is assessed to identify a root cause of plastic response to an internal bodily chemical imbalance or external chemical exposure by performing a lesion study to identify an anatomic target for therapy to target.

In an illustrative example, a cognitive abnormality is assessed to identify a root cause of plastic response to an internal bodily chemical imbalance or external chemical exposure by performing an imaging study to identify an anatomic target for therapy to target.

In an illustrative example, a cognitive abnormality is assessed to identify a root cause of plastic response to an internal bodily chemical imbalance or external chemical exposure by capturing an intrinsic signal of a neurological structure to identify a therapy pattern to block, modulate, interrupt, augment or replace the intrinsic signal.

In an illustrative example, a cognitive abnormality is assessed to identify a root cause of plastic response to an internal bodily chemical imbalance or external chemical exposure by determining a cell or cell population level response to an electrical field or frequency, after determining a cell type for therapeutic assessment, to determine a needed electrical field, temporal or spatial pattern, or frequency for therapy.

In an illustrative example, a cognitive abnormality is assessed to identify a root cause of plastic response to an internal bodily chemical imbalance or external chemical exposure by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a cognitive abnormality is assessed to identify a root cause of plastic response to an internal bodily chemical imbalance or external chemical exposure by determining a therapy parameter effective for a first condition affected by a first neurological target, and translating the therapy parameter for use on a second condition and/or second neurological target.

In an illustrative example, a cognitive abnormality is assessed to identify a root cause of plastic response to an internal bodily chemical imbalance or external chemical exposure by studying an animal model, in vitro model, or in vivo model, to estimate a response for a corresponding or different human anatomical target.

In an illustrative example, a cognitive abnormality is assessed to identify a root cause of plastic response to an internal bodily chemical imbalance or external chemical exposure by using a population study to identify a difference between patients having the patient condition and persons who do not, and aligning the therapy parameters to a measurable difference between the patients and the persons.

In an illustrative example, a cognitive abnormality is assessed to identify a root cause of existence of hyper-excitability or hypo-excitability of a neurological anatomy by performing a lesion study to identify an anatomic target for therapy to target.

In an illustrative example, a cognitive abnormality is assessed to identify a root cause of existence of hyper-excitability or hypo-excitability of a neurological anatomy by performing an imaging study to identify an anatomic target for therapy to target.

In an illustrative example, a cognitive abnormality is assessed to identify a root cause of existence of hyper-excitability or hypo-excitability of a neurological anatomy by capturing an intrinsic signal of a neurological structure to identify a therapy pattern to block, modulate, interrupt, augment or replace the intrinsic signal.

In an illustrative example, a cognitive abnormality is assessed to identify a root cause of existence of hyper-excitability or hypo-excitability of a neurological anatomy by determining a cell or cell population level response to an electrical field or frequency, after determining a cell type for therapeutic assessment, to determine a needed electrical field, temporal or spatial pattern, or frequency for therapy.

In an illustrative example, a cognitive abnormality is assessed to identify a root cause of existence of hyper-excitability or hypo-excitability of a neurological anatomy by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a cognitive abnormality is assessed to identify a root cause of existence of hyper-excitability or hypo-excitability of a neurological anatomy by determining a therapy parameter effective for a first condition affected by a first neurological target, and translating the therapy parameter for use on a second condition and/or second neurological target.

In an illustrative example, a cognitive abnormality is assessed to identify a root cause of existence of hyper-excitability or hypo-excitability of a neurological anatomy by studying an animal model, in vitro model, or in vivo model, to estimate a response for a corresponding or different human anatomical target.

In an illustrative example, a cognitive abnormality is assessed to identify a root cause of existence of hyper-excitability or hypo-excitability of a neurological anatomy by using a population study to identify a difference between patients having the patient condition and persons who do not, and aligning the therapy parameters to a measurable difference between the patients and the persons.

In an illustrative example, a cognitive abnormality is assessed to identify a root cause of overexcitation of a neural pathway by performing a lesion study to identify an anatomic target for therapy to target.

In an illustrative example, a cognitive abnormality is assessed to identify a root cause of overexcitation of a neural pathway by performing an imaging study to identify an anatomic target for therapy to target.

In an illustrative example, a cognitive abnormality is assessed to identify a root cause of overexcitation of a neural pathway by capturing an intrinsic signal of a neurological structure to identify a therapy pattern to block, modulate, interrupt, augment or replace the intrinsic signal.

In an illustrative example, a cognitive abnormality is assessed to identify a root cause of overexcitation of a neural pathway by determining a cell or cell population level response to an electrical field or frequency, after determining a cell type for therapeutic assessment, to determine a needed electrical field, temporal or spatial pattern, or frequency for therapy.

In an illustrative example, a cognitive abnormality is assessed to identify a root cause of overexcitation of a neural pathway by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a cognitive abnormality is assessed to identify a root cause of overexcitation of a neural pathway by determining a therapy parameter effective for a first condition affected by a first neurological target, and translating the therapy parameter for use on a second condition and/or second neurological target.

In an illustrative example, a cognitive abnormality is assessed to identify a root cause of overexcitation of a neural pathway by studying an animal model, in vitro model, or in vivo model, to estimate a response for a corresponding or different human anatomical target.

In an illustrative example, a cognitive abnormality is assessed to identify a root cause of overexcitation of a neural pathway by using a population study to identify a difference between patients having the patient condition and persons who do not, and aligning the therapy parameters to a measurable difference between the patients and the persons.

In an illustrative example, a cognitive abnormality is assessed to identify a root cause of pathological oscillation or synchrony of neurological structures by performing a lesion study to identify an anatomic target for therapy to target.

In an illustrative example, a cognitive abnormality is assessed to identify a root cause of pathological oscillation or synchrony of neurological structures by performing an imaging study to identify an anatomic target for therapy to target.

In an illustrative example, a cognitive abnormality is assessed to identify a root cause of pathological oscillation or synchrony of neurological structures by capturing an intrinsic signal of a neurological structure to identify a therapy pattern to block, modulate, interrupt, augment or replace the intrinsic signal.

In an illustrative example, a cognitive abnormality is assessed to identify a root cause of pathological oscillation or synchrony of neurological structures by determining a cell or cell population level response to an electrical field or frequency, after determining a cell type for therapeutic assessment, to determine a needed electrical field, temporal or spatial pattern, or frequency for therapy.

In an illustrative example, a cognitive abnormality is assessed to identify a root cause of pathological oscillation or synchrony of neurological structures by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a cognitive abnormality is assessed to identify a root cause of pathological oscillation or synchrony of neurological structures by determining a therapy parameter effective for a first condition affected by a first neurological target, and translating the therapy parameter for use on a second condition and/or second neurological target.

In an illustrative example, a cognitive abnormality is assessed to identify a root cause of pathological oscillation or synchrony of neurological structures by studying an animal model, in vitro model, or in vivo model, to estimate a response for a corresponding or different human anatomical target.

In an illustrative example, a cognitive abnormality is assessed to identify a root cause of pathological oscillation or synchrony of neurological structures by using a population study to identify a difference between patients having the patient condition and persons who do not, and aligning the therapy parameters to a measurable difference between the patients and the persons.

In an illustrative example, a cognitive abnormality is assessed to identify a root cause of incorrect or pathological generation, transmission or receipt of neurological, hormonal, visceral or glial signal by performing a lesion study to identify an anatomic target for therapy to target.

In an illustrative example, a cognitive abnormality is assessed to identify a root cause of incorrect or pathological generation, transmission or receipt of neurological, hormonal, visceral or glial signal by performing an imaging study to identify an anatomic target for therapy to target.

In an illustrative example, a cognitive abnormality is assessed to identify a root cause of incorrect or pathological generation, transmission or receipt of neurological, hormonal, visceral or glial signal by capturing an intrinsic signal of a neurological structure to identify a therapy pattern to block, modulate, interrupt, augment or replace the intrinsic signal.

In an illustrative example, a cognitive abnormality is assessed to identify a root cause of incorrect or pathological generation, transmission or receipt of neurological, hormonal, visceral or glial signal by determining a cell or cell population level response to an electrical field or frequency, after determining a cell type for therapeutic assessment, to determine a needed electrical field, temporal or spatial pattern, or frequency for therapy.

In an illustrative example, a cognitive abnormality is assessed to identify a root cause of incorrect or pathological generation, transmission or receipt of neurological, hormonal, visceral or glial signal by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a cognitive abnormality is assessed to identify a root cause of incorrect or pathological generation, transmission or receipt of neurological, hormonal, visceral or glial signal by determining a therapy parameter effective for a first condition affected by a first neurological target, and translating the therapy parameter for use on a second condition and/or second neurological target.

In an illustrative example, a cognitive abnormality is assessed to identify a root cause of incorrect or pathological generation, transmission or receipt of neurological, hormonal, visceral or glial signal by studying an animal model, in vitro model, or in vivo model, to estimate a response for a corresponding or different human anatomical target.

In an illustrative example, a cognitive abnormality is assessed to identify a root cause of incorrect or pathological generation, transmission or receipt of neurological, hormonal, visceral or glial signal by using a population study to identify a difference between patients having the patient condition and persons who do not, and aligning the therapy parameters to a measurable difference between the patients and the persons.

In an illustrative example, a cognitive abnormality is assessed to identify a root cause of presence or absence of a neurological, hormonal, visceral or glial signal to be blocked, modulated, supplemented or replaced by performing a lesion study to identify an anatomic target for therapy to target.

In an illustrative example, a cognitive abnormality is assessed to identify a root cause of presence or absence of a neurological, hormonal, visceral or glial signal to be blocked, modulated, supplemented or replaced by performing an imaging study to identify an anatomic target for therapy to target.

In an illustrative example, a cognitive abnormality is assessed to identify a root cause of presence or absence of a neurological, hormonal, visceral or glial signal to be blocked, modulated, supplemented or replaced by capturing an intrinsic signal of a neurological structure to identify a therapy pattern to block, modulate, interrupt, augment or replace the intrinsic signal.

In an illustrative example, a cognitive abnormality is assessed to identify a root cause of presence or absence of a neurological, hormonal, visceral or glial signal to be blocked, modulated, supplemented or replaced by determining a cell or cell population level response to an electrical field or frequency, after determining a cell type for therapeutic assessment, to determine a needed electrical field, temporal or spatial pattern, or frequency for therapy.

In an illustrative example, a cognitive abnormality is assessed to identify a root cause of presence or absence of a neurological, hormonal, visceral or glial signal to be blocked, modulated, supplemented or replaced by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a cognitive abnormality is assessed to identify a root cause of presence or absence of a neurological, hormonal, visceral or glial signal to be blocked, modulated, supplemented or replaced by determining a therapy parameter effective for a first condition affected by a first neurological target, and translating the therapy parameter for use on a second condition and/or second neurological target.

In an illustrative example, a cognitive abnormality is assessed to identify a root cause of presence or absence of a neurological, hormonal, visceral or glial signal to be blocked, modulated, supplemented or replaced by studying an animal model, in vitro model, or in vivo model, to estimate a response for a corresponding or different human anatomical target.

In an illustrative example, a cognitive abnormality is assessed to identify a root cause of presence or absence of a neurological, hormonal, visceral or glial signal to be blocked, modulated, supplemented or replaced by using a population study to identify a difference between patients having the patient condition and persons who do not, and aligning the therapy parameters to a measurable difference between the patients and the persons.

In an illustrative example, a cognitive abnormality is assessed to identify a root cause of presence or absence of sympathetic or parasympathetic nervous system responses by performing a lesion study to identify an anatomic target for therapy to target.

In an illustrative example, a cognitive abnormality is assessed to identify a root cause of presence or absence of sympathetic or parasympathetic nervous system responses by performing an imaging study to identify an anatomic target for therapy to target.

In an illustrative example, a cognitive abnormality is assessed to identify a root cause of presence or absence of sympathetic or parasympathetic nervous system responses by capturing an intrinsic signal of a neurological structure to identify a therapy pattern to block, modulate, interrupt, augment or replace the intrinsic signal.

In an illustrative example, a cognitive abnormality is assessed to identify a root cause of presence or absence of sympathetic or parasympathetic nervous system responses by determining a cell or cell population level response to an electrical field or frequency, after determining a cell type for therapeutic assessment, to determine a needed electrical field, temporal or spatial pattern, or frequency for therapy.

In an illustrative example, a cognitive abnormality is assessed to identify a root cause of presence or absence of sympathetic or parasympathetic nervous system responses by determining a response to a drug or chemical interaction to identify an anatomic target and one or more electrical characteristics of a binding or receiving structure of an anatomic target, such that therapy can be selected to stimulate or block the binding or receiving structure.

In an illustrative example, a cognitive abnormality is assessed to identify a root cause of presence or absence of sympathetic or parasympathetic nervous system responses by determining a therapy parameter effective for a first condition affected by a first neurological target, and translating the therapy parameter for use on a second condition and/or second neurological target.

In an illustrative example, a cognitive abnormality is assessed to identify a root cause of presence or absence of sympathetic or parasympathetic nervous system responses by studying an animal model, in vitro model, or in vivo model, to estimate a response for a corresponding or different human anatomical target.

In an illustrative example, a cognitive abnormality is assessed to identify a root cause of presence or absence of sympathetic or parasympathetic nervous system responses by using a population study to identify a difference between patients having the patient condition and persons who do not, and aligning the therapy parameters to a measurable difference between the patients and the persons.

The word physician as such should not be read as a restriction on the actual title or background of any person. While several of these examples make reference to a physician actor, it should be understood that this term can encompass persons acting at the direction of a physician (such as a nurse, physician's assistant or company representative). In addition, reference to a physician identifying conditions and establishing links to parameters may include reference to non-physician or non-practitioner researchers, such as students, professors and other field subject matter experts who may guide or direct research efforts.

A first non-limiting example takes the form of a neuromodulation device configured for use with one or more electrodes for delivery of neuromodulation signals, the device comprising: therapy means for delivering therapy via the one or more electrodes; first means to control the therapy means to deliver a first therapy pattern to accomplish a first effect on a patient; second means to control the therapy means to deliver a second therapy pattern to accomplish a second effect on a patient; wherein the first and second means are configured to automatically pass control from one to the other, such that the first effect is impacts the second effect; and wherein the first and second patterns are different from one another. A therapy means circuitry is shown and described above in several forms and may include voltage controlled sources, current controlled sources, switches or multiplexors to select various electrodes for use in anode and/or cathode roles; an example is shown in detail in FIG. 5. Various patterns that may be used are shown throughout FIGS. 6-11, and FIG. 11 in particular illustrates the delivery of multiple patterns in sequence. FIGS. 12-13 show examples of stored instruction sets with separate sets of instructions for controlling therapy output circuitry according to different patterns.

A second non-limiting example takes the form of a device as in the first non-limiting example, wherein the first effect is a blocking effect and the second effect is a subthreshold effect, and the first pattern and second pattern are configured to use different subsets of the one or more electrodes to accomplish the first effect and second effect in different volumes of patient tissue. A third non-limiting example takes the form of a device as in the first non-limiting example, wherein the first effect is a blocking effect and the second effect is a stimulation effect, and the first pattern and second pattern are configured to use different subsets of the one or more electrodes to accomplish the first effect and second effect in different volumes of patient tissue. A fourth non-limiting example takes the form of a device as in the first non-limiting example, wherein the first effect is a hyperpolarization effect and the second effect is a stimulation effect, and the first pattern and second pattern are configured to use different subsets of the one or more electrodes to accomplish the first effect and second effect in different volumes of patient tissue.

A fifth non-limiting example takes the form of a device as in the first non-limiting example, wherein the first effect is a subthreshold effect and the second effect is a stimulation effect, and the first pattern and second pattern are configured to use different subsets of the one or more electrodes to accomplish the first effect and second effect in different volumes of patient tissue. A sixth non-limiting example takes the form of a device as in the first non-limiting example, wherein the first effect is a stimulation effect and the second effect is also a stimulation effect, and the first pattern and second pattern are configured to use different subsets of the one or more electrodes to accomplish the first effect and second effect in different volumes of patient tissue, wherein the first effect impacts the second effect by interfering with propagation of the stimulation effect. A seventh non-limiting example takes the form of a device as in the first non-limiting example, wherein the first effect is a blocking effect and the second effect is a hyperpolarization effect, and the first pattern and second pattern are configured to use different subsets of the one or more electrodes to accomplish the first effect and second effect in different volumes of patient tissue.

An eighth non-limiting example takes the form of a device as in the first non-limiting example, wherein the first effect is a subthreshold effect and the second effect is a hyperpolarization effect, and the first pattern and second pattern are configured to use different subsets of the one or more electrodes to accomplish the first effect and second effect in different volumes of patient tissue. A ninth non-limiting example takes the form of a device as in the first non-limiting example, wherein the first effect is a blocking effect and the second effect is a blocking effect, and the first pattern and second pattern are configured to use different subsets of the one or more electrodes to accomplish the first effect and second effect in different volumes of patient tissue. A tenth non-limiting example takes the form of a device as in the first non-limiting example, wherein the first effect is a subthreshold effect and the second effect is a subthreshold effect, and the first pattern and second pattern are configured to use different subsets of the one or more electrodes to accomplish the first effect and second effect in different volumes of patient tissue. An eleventh non-limiting example takes the form of a device as in the first non-limiting example, wherein the first effect is a hyperpolarization effect and the second effect is a hyperpolarization effect, and the first pattern and second pattern are configured to use different subsets of the one or more electrodes to accomplish the first effect and second effect in different volumes of patient tissue.

A twelfth non-limiting example takes the form of a device as in any of the first to eleventh non-limiting examples, wherein the first and second effects are selected so as to modulate operation of a neural network of a patient in at least two separate spatial ways. For example, a first pattern may be chosen using first and second electrodes to achieve a first effect (such as hyperpolarization, subthreshold, excitation, or blocking) at a first location near the first and second electrodes, and a second pattern may be chosen using third and fourth electrodes to achieve a second effect (such as hyperpolarization, subthreshold, excitation, or blocking) at a first location near the third and fourth electrodes.

A thirteenth non-limiting example takes the form of a device as in any of the first to eleventh non-limiting examples, wherein the first and second effects are selected so as to modulate operation of a neural network in at least two separate temporal ways. For example a first pattern may be delivered at a first point in time to achieve a first effect (such as hyperpolarization, subthreshold, excitation, or blocking) which remains while the second pattern is delivered subsequently at a second point in time to achieve a second effect (such as hyperpolarization, subthreshold, excitation, or blocking).

A fourteenth non-limiting example takes the form of a device as in any of the first to eleventh non-limiting examples, wherein the first and second effects are selected so as to modulate activity of a neural network in both temporally and spatially diverse manners. For example, a first pattern may be chosen using first and second electrodes to achieve a first effect (such as hyperpolarization, subthreshold, excitation, or blocking) at a first location near the first and second electrodes and delivered at a first point in time, and a second pattern may be chosen using third and fourth electrodes to achieve a second effect (such as hyperpolarization, subthreshold, excitation, or blocking) at a first location near the third and fourth electrodes and delivered at a second point in time subsequent to the first point in time such that the first effect causes the second effect to be different from, or have a different result from, what would occur if the first pattern had not been delivered.

A fifteenth non-limiting example takes the form of a device as in any of the first to fourteenth non-limiting examples, taking the form of an implantable neurostimulator comprising a housing and operational circuitry in the housing, the housing including one or more ports for coupling to an implantable lead having a plurality of stimulus deliver electrodes thereon, the operational circuitry comprising a controller or processor coupled to a memory, wherein the operational circuitry comprises one or more components that make up the therapy means, and the first and second means to control the therapy means include operational instructions stored by the memory and operated at least in part by the controller or processor. Such devices are shown in system form in FIGS. 1 to 4, with schematic representations shown for internal operational circuitry in FIG. 5.

A sixteenth non-limiting example takes the form of a neuromodulation device configured for use with one or more electrodes for delivery of neuromodulation signals, and having operational circuitry including therapy delivery circuitry controllable by the operational circuitry, wherein the operational circuitry is configured to control the therapy delivery circuitry to have at least the following therapeutic outputs programmed: a first therapy pattern configured to accomplish a first effect on a patient; a second therapy pattern configured to accomplish a second effect on a patient; wherein the operational circuitry is configured to output the first therapy pattern and the second therapy pattern such that the first effect is impacts the second effect; and wherein the first and second patterns are different from one another.

A seventeenth non-limiting example takes the form of a device as in the sixteenth non-limiting example, wherein the first effect is a blocking effect and the second effect is a subthreshold effect, and the first pattern and second pattern are configured to use different subsets of the one or more electrodes to accomplish the first effect and second effect in different volumes of patient tissue. An eighteenth non-limiting example takes the form of a device as in the sixteenth non-limiting example, wherein the first effect is a blocking effect and the second effect is a stimulation effect, and the first pattern and second pattern are configured to use different subsets of the one or more electrodes to accomplish the first effect and second effect in different volumes of patient tissue. A nineteenth non-limiting example takes the form of a device as in the sixteenth non-limiting example, wherein the first effect is a hyperpolarization effect and the second effect is a stimulation effect, and the first pattern and second pattern are configured to use different subsets of the one or more electrodes to accomplish the first effect and second effect in different volumes of patient tissue.

A twentieth non-limiting example takes the form of a device as in the sixteenth non-limiting example, wherein the first effect is a subthreshold effect and the second effect is a stimulation effect, and the first pattern and second pattern are configured to use different subsets of the one or more electrodes to accomplish the first effect and second effect in different volumes of patient tissue. A twenty-first non-limiting example takes the form of a device as in the sixteenth non-limiting example, wherein the first effect is a stimulation effect and the second effect is also a stimulation effect, and the first pattern and second pattern are configured to use different subsets of the one or more electrodes to accomplish the first effect and second effect in different volumes of patient tissue, wherein the first effect impacts the second effect by interfering with propagation of the stimulation effect. A twenty-second non-limiting example takes the form of a device as in the sixteenth non-limiting example, wherein the first effect is a blocking effect and the second effect is a hyperpolarization effect, and the first pattern and second pattern are configured to use different subsets of the one or more electrodes to accomplish the first effect and second effect in different volumes of patient tissue.

A twenty-third non-limiting example takes the form of a device as in the sixteenth non-limiting example, wherein the first effect is a subthreshold effect and the second effect is a hyperpolarization effect, and the first pattern and second pattern are configured to use different subsets of the one or more electrodes to accomplish the first effect and second effect in different volumes of patient tissue. A twenty-fourth non-limiting example takes the form of a device as in the sixteenth non-limiting example, wherein the first effect is a blocking effect and the second effect is a blocking effect, and the first pattern and second pattern are configured to use different subsets of the one or more electrodes to accomplish the first effect and second effect in different volumes of patient tissue. A twenty-fifth non-limiting example takes the form of a device as in the sixteenth non-limiting example, wherein the first effect is a subthreshold effect and the second effect is a subthreshold effect, and the first pattern and second pattern are configured to use different subsets of the one or more electrodes to accomplish the first effect and second effect in different volumes of patient tissue.

A twenty-sixth non-limiting example takes the form of a device as in the sixteenth non-limiting example, wherein the first effect is a hyperpolarization effect and the second effect is a hyperpolarization effect, and the first pattern and second pattern are configured to use different subsets of the one or more electrodes to accomplish the first effect and second effect in different volumes of patient tissue. A twenty-seventh non-limiting example takes the form of a device as in any of the sixteenth to twenty-fifth non-limiting examples, wherein the first and second effects are selected so as to modulate operation of a neural network of a patient in at least two separate spatial ways. A twenty-eighth non-limiting example takes the form of a device as in any of the sixteenth to twenty-fifth non-limiting examples, wherein the first and second effects are selected so as to modulate operation of a neural network in at least two separate temporal ways. A twenty-ninth non-limiting example takes the form of a device as in any of the sixteenth to twenty-fifth non-limiting examples, wherein the first and second effects are selected so as to modulate activity of a neural network in both temporally and spatially diverse manners.

A thirtieth non-limiting example takes the form of a device as in any of the sixteenth to twenty-ninth non-limiting examples, taking the form of an implantable neurostimulator comprising a housing and operational circuitry in the housing, the housing including one or more ports for coupling to an implantable lead having a plurality of stimulus deliver electrodes thereon, the operational circuitry comprising a controller or processor coupled to a memory.

A thirty-first non-limiting example takes the form of a method of operation using a neurostimulation system including a stimulation generator for applying stimulation to a patient and a programming apparatus for use with the stimulation generator, the method comprising: identifying a patient condition requiring treatment; linking the patient condition to one or more therapy parameters; programming the therapy apparatus, using the programmer, to deliver therapy in accordance with the one or more therapy parameters; testing the therapy parameter in a patient having the patient condition using the neurostimulation device to deliver therapy using the one or more therapy parameters; and determining a result from the testing step, including whether the therapy regimen was significant in modulating the patient condition.

A thirty-second non-limiting example takes the form of a method as in the thirty-first non-limiting example, wherein the step of linking the patient condition to one or more therapy parameters comprises identifying a plurality of therapy targets within the patient and defining a sequence of therapy steps to provide for the plurality of therapy targets, wherein the one or more therapy parameters generate the sequence of therapy steps.

A thirty-third non-limiting example takes the form of a method as in the thirty-first non-limiting example, wherein the step of linking the patient condition to one or more therapy parameters comprises identifying a biological characteristic of a cell type or a component thereof, and defining a therapy waveform configured to modulate behavior of the cell type using the biological characteristic.

A thirty-fourth non-limiting example takes the form of a method as in the thirty-third non-limiting example, wherein the biological characteristic is a frequency at which the cell type is susceptible to modulation of behavior, and the therapy waveform is configured based on the frequency. A thirty-fifth non-limiting example takes the form of a method as in the thirty-fourth non-limiting example, wherein the therapy waveform includes one or more components comprising a signal for which a threshold proportion of the waveform energy is carried in a band or bands about the frequency.

A thirty-sixth non-limiting example takes the form of a method as in the thirty-third non-limiting example, wherein the biological characteristic is an excitation threshold, and the therapy waveform is configured in order to exceed the excitation threshold. A thirty-seventh non-limiting example takes the form of a method as in the thirty-third non-limiting example, wherein the biological characteristic is an excitation threshold, and the therapy waveform is configured to deliver a subthreshold stimulus without exceeding the excitation threshold. A thirty-eighth non-limiting example takes the form of a method as in the thirty-third non-limiting example, wherein the biological characteristic is a resting membrane potential, and the therapy waveform is configured to hyperpolarize one or more cells. A thirty-ninth non-limiting example takes the form of a method as in the thirty-third non-limiting example, wherein the biological characteristic is a combination of stimulus input characteristics sufficient to electrically block one or more cells of the patient's neurological system.

A fortieth non-limiting example takes the form of a method as in the thirty-first non-limiting example, wherein the step of linking the patient condition to one or more therapy parameters comprises identifying a network of cells that is comprised at least in part of neurons, and defining a therapy output to affect operation of the neural network.

A forty-first non-limiting example takes the form of a method as in the fortieth non-limiting example, wherein the therapy output is configured to cause the neural network to operate in a first manner rather than a second manner. A forty-second non-limiting example takes the form of a method as in the fortieth non-limiting example, wherein the therapy output is configured to increase excitability of a one or more cells in the network. A forty-third non-limiting example takes the form of a method as in the fortieth non-limiting example wherein the therapy output is configured to hyperpolarize one or more cells in the network.

A forty-fourth non-limiting example takes the form of a method as in the fortieth non-limiting example wherein the therapy output is configured to facilitate connectivity between two parts of the network. A forty-fifth non-limiting example takes the form of a method as in the fortieth non-limiting example, wherein the therapy output is configured to isolate two parts of the network. A forty-sixth non-limiting example takes the form of a method as in the fortieth non-limiting example, wherein the therapy output comprises at least first and second patterns delivered to target at least first and second different locations in the network. A forty-seventh non-limiting example takes the form of a method as in the fortieth non-limiting example, wherein the therapy output comprises at least first and second patterns delivered at different times and at least first and second different locations in the network. A forty-eighth non-limiting example takes the form of a method as in the fortieth non-limiting example, wherein the step of determining a result includes observing signaling at several locations in the network.

A forty-ninth non-limiting example takes the form of a method as in the thirty-first non-limiting example, wherein the step of linking the patient condition to one or more therapy parameters comprises identifying a characteristic of an extracellular medium, wherein the one or more therapy parameters are selected to affect the extracellular medium.

A fiftieth non-limiting example takes the form of a method as in the thirty-first non-limiting example, wherein the step of linking the patient condition to one or more therapy parameters comprises identifying a first biological characteristic of a first cell type, and a identifying a second biological characteristic of a second cell type, wherein the therapy parameters are selected to modulating the first cell type without modulating the second cell type.

A fifty-first non-limiting example takes the form of a method as in the thirty-first non-limiting example, wherein the step of linking the patient condition to one or more therapy parameters comprises: identifying a first neurological structure associated with the patient condition; measuring, estimating, or identifying a minimum electrical field necessary to modulate the first neurological structure; identifying a spatial relationship between one or more therapy delivery electrodes and the first neurological structure; and determining an output necessary to generate the minimum electrical field based on the spatial relationship.

A fifty-second non-limiting example takes the form of a method as in the fifty-first non-limiting example wherein the step of linking the patient condition to one or more therapy parameters comprises: identifying a second neurological structure associated with a side effect of the therapy parameters; measuring, estimating, or identifying a minimum electrical field necessary to stimulate the second neurological structure; identifying a spatial relationship between one or more therapy delivery electrodes and the second neurological structure; determining an output necessary to stimulate the second neurological structure in a manner to minimize the side effect.

A fifty-third non-limiting example takes the form of a method as in the thirty-first non-limiting example, wherein the step of linking the patient condition to one or more therapy parameters comprises: identifying a first neurological structure associated with the patient condition; measuring, estimating, or identifying a minimum electrical current necessary to modulate the first neurological structure; identifying a spatial relationship between one or more therapy delivery electrodes and the first neurological structure; determining an output necessary to generate the minimum electrical current based on the spatial relationship.

A fifty-fourth non-limiting example takes the form of a method as in the fifty-third non-limiting example, wherein the step of linking the patient condition to one or more therapy parameters comprises: identifying a second neurological structure associated with a side effect of the therapy parameters; measuring, estimating, or identifying a minimum electrical field necessary to stimulate the second neurological structure; identifying a spatial relationship between one or more therapy delivery electrodes and the second neurological structure; determining an output necessary to stimulate the second neurological structure in a manner to minimize the side effect.

A fifty-fifth non-limiting example takes the form of a method as in the thirty-first non-limiting example, further comprising: if the result is significant in modulating the patient condition, uploading a set of information to a neurostimulation library via the programming apparatus, the set of information including: one or more items of information related to the patient condition; and one or more items of information related to the therapy parameters. The information uploaded or conveyed may include expected therapeutic and/or side-effects of the therapy.

A fifty-sixth non-limiting example takes the form of a method as in the thirty-first non-limiting example, further comprising: if the result is not significant in modulating the patient condition, uploading a set of information to a neurostimulation library via the programming apparatus, the set of information including: one or more items of information related to the patient condition; and one or more items of information related to the therapy parameters. Upload of non-significant-result producing data may assist in ruling out certain patterns or in identifying further potential therapies to test.

A fifty-seventh non-limiting example takes the form of a method as in the thirty-first non-limiting example, wherein the neurostimulation device is configured as a signal generator facilitating delivery of a discretized series of individual therapy pulses each having a duration and amplitude subject to a set of therapy safety rules. A fifty-eighth non-limiting example takes the form of a method as in the thirty-first non-limiting example, wherein the neurostimulation device is configured as a quasi-arbitrary function generator for playing a program made up of a discretized series of individual pulses having a duration and a magnitude, which facilitates independent output within the series such that a first pulse having a first duration and magnitude does not place limitations on a second, subsequent pulse.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A neuromodulation device configured for use with one or more electrodes for delivery of neuromodulation signals, and having operational circuitry including therapy delivery circuitry controllable by the operational circuitry, wherein the operational circuitry is configured to control the therapy delivery circuitry to have at least the following therapeutic outputs programmed:
   a first therapy pattern configured to accomplish a first effect on a patient;
   a second therapy pattern configured to accomplish a second effect on a patient;
   wherein the operational circuitry is configured to output the first therapy pattern and the second therapy pattern using a plurality of the electrodes such that the first effect impacts the second effect; and
   wherein the first and second patterns are different from one another insofar as the first therapy pattern is an asymmetric voltage controlled output, and the second therapy pattern is an assymetric current controlled output.

2. The device of claim 1 wherein the first effect is a hyperpolarization effect and the second effect is a stimulation effect, and the first pattern and second pattern are configured to use different subsets of the one or more electrodes to accomplish the first effect and second effect in different volumes of patient tissue.

3. The device of claim 1 wherein the first effect is a subthreshold effect and the second effect is a stimulation effect, and the first pattern and second pattern are configured to use different subsets of the one or more electrodes to accomplish the first effect and second effect in different volumes of patient tissue.

4. The device of claim 1 wherein the first effect is a stimulation effect and the second effect is also a stimulation effect, and the first pattern and second pattern are configured to use different subsets of the one or more electrodes to accomplish the first effect and second effect in different volumes of patient tissue, wherein the first effect impacts the second effect by interfering with propagation of the stimulation of the second effect.

5. The device of claim 1 wherein the first effect is a blocking effect and the second effect is a hyperpolarization effect, and the first pattern and second pattern are configured to use different subsets of the one or more electrodes to accomplish the first effect and second effect in different volumes of patient tissue.

6. The device of claim 1 wherein the first effect is a subthreshold effect and the second effect is a hyperpolarization effect, and the first pattern and second pattern are configured to use different subsets of the one or more electrodes to accomplish the first effect and second effect in different volumes of patient tissue.

7. The device of claim 1 wherein the first and second effects are selected so as to modulate operation of a neural network of a patient in at least two separate spatial ways.

8. The device of claim 1 wherein the first and second effects are selected so as to modulate operation of a neural network in at least two separate temporal ways.

9. The device of claim 1 wherein the first and second effects are selected so as to modulate activity of a neural network in both temporally and spatially diverse manners.

10. The device of claim 1, taking the form of an implantable neurostimulator comprising a housing containing the operational circuitry, the housing including one or more ports for coupling to an implantable lead having a plurality of stimulus delivery electrodes thereon, the operational circuitry comprising a controller or processor coupled to a memory.

11. The device of claim 1 wherein the operational circuitry is configured to monitor charge delivered during each of the first and second therapy patterns and to then generate one or more asymmetric closing pulses configured to avoid long term polarization of tissue-electrode interfaces of the plurality of electrodes after delivery of one or more iterations of the first and second therapy patterns.

12. The device of claim 11 wherein the operational circuitry is configured to deliver the closing pulse or pulses in a subthreshold manner.

13. The device of claim 11 wherein the operational circuitry is configured to deliver the closing pulse or pulses in a hyperpolarizing manner.

14. A method of operating a neuromodulation device configured for use with one or more electrodes for delivery of neuromodulation signals, and having operational circuitry including therapy delivery circuitry controllable by the operational circuitry, wherein the method comprises delivering the following therapeutic outputs:
a first therapy pattern configured to accomplish a first effect on a patient; and
a second therapy pattern configured to accomplish a second effect on a patient;
the therapy outputs using a plurality of electrodes such that the first effect impacts the second effect; and
wherein the first and second patterns are different from one another insofar as the first therapy pattern is an asymmetric voltage controlled output, and the second therapy pattern is an asymmetric current controlled output.

15. The method of claim 14, wherein the first effect is a subthreshold effect and the second effect is a stimulation effect, and the first pattern and second pattern are delivered by using different subsets of the one or more electrodes to accomplish the first effect and second effect in different volumes of patient tissue.

16. The method of claim 14, wherein the first and second effects are selected so as to modulate operation of a neural network in at least two separate temporal ways.

17. The method of claim 14, wherein the device takes the form of an implantable neurostimulator comprising a housing that contains the operational circuitry and including one or more ports for coupling to an implantable lead having a plurality of stimulus delivery electrodes thereon, the operational circuitry comprising a controller or processor coupled to a memory.

18. The method of claim 14, further comprising monitoring charge delivered during delivery of each of the first and second therapy patterns, and generating one or more asymmetric closing pulses configured to avoid long term polarization of tissue-electrode interfaces of the plurality of electrodes after delivery of one or more iterations of the first and second therapy patterns.

19. The method of claim 18 wherein the closing pulse or pulses is delivered in a subthreshold manner.

20. The method of claim 18 wherein the closing pulse or pulses is delivered in a hyperpolarizing manner.

* * * * *